US007372039B2

(12) United States Patent
Tokhtuev et al.

(10) Patent No.: US 7,372,039 B2
(45) Date of Patent: May 13, 2008

(54) NEAR UV ABSORPTION SPECTROMETER AND METHOD FOR USING THE SAME

(75) Inventors: Eugene Tokhtuev, Duluth, MN (US); Christopher J. Owen, Duluth, MN (US); Paul Schilling, Duluth, MN (US); Anna Pilipchenko, Duluth, MN (US); Paul R. Kraus, Apple Valley, MN (US); Katherine M. Sanville, White Bear Lake, MN (US)

(73) Assignee: Ecolab Inc., St. Paul, MN (US)

( * ) Notice: Subject to any disclaimer, the term of this patent is extended or adjusted under 35 U.S.C. 154(b) by 70 days.

(21) Appl. No.: 11/311,126

(22) Filed: Dec. 20, 2005

(65) Prior Publication Data

US 2007/0138401 A1  Jun. 21, 2007

(51) Int. Cl.
    *G01J 1/42* (2006.01)
(52) U.S. Cl. .................. 250/373; 250/372; 250/356.1
(58) Field of Classification Search ................ 250/373, 250/372, 356, 356.1
    See application file for complete search history.

(56) References Cited

U.S. PATENT DOCUMENTS

| | | | |
|---|---|---|---|
| 5,394,237 A * | 2/1995 | Chang et al. ............... 356/328 |
| 5,420,432 A * | 5/1995 | Manook et al. ............. 250/373 |
| 5,864,140 A * | 1/1999 | Owens ........................ 250/343 |
| 2003/0141458 A1* | 7/2003 | Ross et al. ................ 250/458.1 |

OTHER PUBLICATIONS

Relative error. (1992). In Academic Press Dictionary of Science and Technology. Retrieved Jun. 25, 2007, from http://www.credoreference.com/entry/3150964.*
J. M. Broomhead et al., "Crystal Structures of Zinc and Magnesium Benzene Sulphonates", Nature, vol. 160, No. 4075, Dec. 6, 1947, p. 795.
S. R. Epton, "A Rapid Method of Analysis for Certain Surface—Active Agents", Nature, vol. 160, No. 4075, Dec. 6, 1947, pp. 795-796.
M. L. Sapiro, "Reaction of Nitrous Acid with Chlorophyll", Nature, vol. 160, No. 4075, Dec. 6, 1947, p. 796.
S. R. Epton, "A New Method for the Rapid Titrimetric Analysis of Sodium Alkyl Sulphates and Related Compounds", Analysis of Sodium Alkyl Sulphates, Etc., Jan. 29, 1947, pp. 226-230.

* cited by examiner

*Primary Examiner*—David Porta
*Assistant Examiner*—Jessica L Eley
(74) *Attorney, Agent, or Firm*—Shumaker & Sieffert, P.A.

(57) ABSTRACT

A UV absorption spectrometer includes a housing, a controller, and a sensor unit including an ultraviolet light source, an analytical area in an analytical cell or in running water or gaseous medium, and an UV wavelength separator including a UV detector. An ultraviolet light in a wavelength range of 200-320 nm emits from the light source through the analytical area to the wavelength separator, and the controller transforms output signals from the UV detector into absorbance values or optical densities for two or more wavelengths in the wavelength range, calculates differences of said absorbance values or optical densities, determines a concentration of a chemical in the solution with calibration constants found for a known concentration of the chemical and said differences of said absorbance values or optical densities.

35 Claims, 22 Drawing Sheets

NEAR UV ABSORPTION SPECTROMETER AND METHOD FOR USING THE SAME

BACKGROUND OF THE INVENTION

1. Field of the Invention

The invention generally relates to a portable absorption spectrometer for testing a liquid sample, and more particularly to a near UV absorption spectrometer for determining and monitoring chemicals, especially biocide, in solutions or running water or the like.

2. Description of Related Arts

A biocide is a chemical substance, such as pesticides, which can be fungicides, herbicides, insecticides, miticides, or rodenticides, etc., capable of killing different forms of living organisms used in fields such as agriculture, forestry, and mosquito control. Biocides can also be added to other materials (typically liquids) to protect the material from biological infestation and growth. For example, certain types of quats can be added to pool water or industrial water systems to act as an algicide, protecting the water from infestation and growth of algae. Chlorine can be added in low concentrations to water as one of the final steps in wastewater treatment as a general biocide to kill microorganisms, algae, etc. Adding hypochlorite solutions to pools, etc. to gradually release hypochlorite and chlorine into the water. Compounds such as sodium dichloro-s-triazinetrione (dihydrate or anhydrous), sometimes referred to as dichlor, and trichloro-s-triazinetrione, sometimes referred to as trichlor, are even more convenient to use. These compounds are stable while solid and may be used in powdered, granular, or tablet form. When added in small amounts to pool water or industrial water systems, the chlorine atoms hydrolyze from the rest of the molecule forming hypochlorous acid (HOCl) which acts as a general biocide killing germs, micro-organisms, algae, etc. Chlorinated hydantoin compounds are also used as biocides.

Restaurants soak and wash cooking ware and silverware in detergents, then rinse away the detergents with water. Thereafter, the ware is soaked in and sanitized with a sanitizing solution. The detergent is a compound, or a mixture of compounds to assist cleaning. Such a substance, especially those made for use with water, may include any of various components having several properties: surfactants to "cut" grease and to wet surfaces, abrasives to scour substances to modify pH, either to affect performance or stability of other ingredients, or as caustics to destroy dirt, water "softeners" to counteract the effect of "hardness" ions on other ingredients, oxidants (oxidizers) for bleaching and destruction of dirt materials other than surfactants to keep dirt in suspension, enzymes to digest proteins, fats, or carbohydrates in dirt or to modify fabric feel ingredients, surfactant or otherwise, modifying the foaming properties of the cleaning surfactants, to either stabilize or counteract foam plus ingredients having other properties to go along with detergency, such as fabric brighteners, softeners, etc., and colors, perfumes, etc. Quaternary ammonium cations (QAC), also known as quats, are commonly used as sanitizer and have positively charged polyatonaic ions of the structure $NR_4^+$ with R being alkyl groups. Unlike the ammonium ion $NH_4^+$ itself and primary, secondary, or tertiary ammonium cations, the quaternary ammonium cations are permanently charged, independent of the pH of their solution. Quats in a sanitizing solution are gradually decreased by their combination with the residual detergent. There are legal requirements for the quats concentration in the sanitizing solution to safeguard public health. Inspectors form public health authorities visit restaurants to test with a disposable testing kit or paper so as to ensure the restaurants comply with the concentration standard. If not, the restaurants will be fined. Currently, restaurants dispose of the sanitizing solution either after a certain number of times of use, or after periodic testing shows the quats concentration drops below the standard.

There is a need for a device and method for automatically and economically testing the sanitizing solution for quats concentration.

The prior art applies acid-base titration to measure concentration of quats which makes use of the neutralization reaction that occurs between acids and bases. First of all, a burette should be rinsed with the standard solution, a pipette with the quats solution, and the conical flask with distilled water. Secondly, a known volume of the quats solution is taken with the pipette and placed into the conical flask, along with a small amount of the indicator. The burette should be filled to the top of its scale with the known solution. The known solution is allowed out of the burette, into the conical flask. At this stage, conducting a rough estimate of the amount of this solution it took to neutralize the quats solution. Let the solution out of the burette until the indicator changes color and then record the value on the burette. This is the first titre and should be discluded from any calculations. When all quats have reacted, the solution will have a pH dependant on the relative strengths of the acids and bases. A Quat indicator is in a deprotenated form, and hence carries a negative charge. It thus associates with the quat (a positive ion) to form a complex which changes the pH, the pi electrons' environment and hence the color of the indicator. Then, when all the quats are titrated, the indicators are no longer associated with the quats thus revert to the color they would be in a normal pH~7 solution (violet/blue and orange, which makes gray).

There are other techniques used to quantify the concentration of QACs. One technique is a procedure developed by Epton which involves a dye-transfer in immiscible solvents, usually chloroform and water. An anionic surfactant such as sodium dodecyl sulfate is used as the titrant and an anionic dye, methylene blue for example, is used to indicate the titration endpoint when the dye transfers color from one phase to the other. The use of chloroform is discouraged because of its toxicity and this technique is not generally used in field applications. References to the original method developed by Epton are: S. Epton, Nature, 160, 795 (1947) S. Epton, Trans, Faraday Soc., 44, 226 (1948).

Another method is the direct titration with sodium tetraphenylborate. QACs suppress the acid color (red) of methyl orange. The addition of sodium tetraphenylborate complexes the QAC and makes the dye color visible. Bromophenol blue exhibits a similar response mechanism turning purple at the endpoint of the titration.

A halide determination is also used to determine the QAC concentration. QACs are cationic molecules with a negatively charged counter ion such as chloride (a member of the halide group in the periodic table). One such halide determination technique for QACs precipitates chloride from acidified QAC solution using silver nitrate. The sample is filtered after the addition of silver nitrate and the filtrate is titrated with ammonium thiocyanate in the presence of ferric ammonium sulfate (Volhard indicator) to the first appearance of pink.

Metrohm AG is a company that specialized in ion analysis describes a method that employs a surfactant ion selective electrode (ISE). The ISE is a liquid membrane electrode optimized for ionic surfactants through careful control of the ionophore/plasticizer that makes-up the electrode membrane. The potential generated by the ISE and reference electrodes is proportional to the concentration of the QAC in the sample, following the Nernst equation; $E=E_0+k \cdot \log(C)$. In this equation k is a proportionality constant and is ideally 59 mV per decade concentration for monovalent ions at 25°

C. Titration of the QAC may use an anionic surfactant such as sodium dodecyl sulfate as the titrant. A plot of titrant volume versus ISE voltage yields an inflection point at the endpoint of the titration.

There is a need to directly measure/monitor the concentration of quats automatically, economically, continuously, and with a high sensitivity.

Absorption spectroscopy uses the range of electromagnetic spectra in which a substance absorbs. In atomic absorption spectroscopy, the sample is atomized and then light of a particular frequency is passed through the vapor. After calibration, the amount of absorption can be related to the concentrations of various metal ions through the Beer-Lambert law. The method can be automated and is widely used to measure concentrations of ions such as sodium and calcium in blood. Other types of spectroscopy may not require sample atomization. For example, ultraviolet/visible (UV/Vis) absorption spectroscopy is most often performed on liquid samples to detect molecular content, and infrared (IR) spectroscopy is most often performed on liquid, semi-liquid (paste or grease), dried, or solid samples to determine molecular information, including structural information. Ultraviolet-Visible Spectroscopy or Ultraviolet-Visible Spectrophotometry (UV/VIS) involves the spectroscopy of photons (spectrophotometry). It uses light in the visible and adjacent near ultraviolet (UV) and near infrared (NIR) ranges. In this region of energy space molecules undergo electronic transitions.

An ultraviolet spectrum is essentially a graph (or plot) of light absorbance vs. wavelength in a range of ultraviolet. Similarly, for a given material of species, such as quats, a standard graph of extinction coefficient $\epsilon$ vs. wavelength is available. Such a standard graph would be effectively "concentration-corrected" and thus independent of concentration.

The measured variable is often the light intensity but could also be the polarization state, for instance. The independent variable is often the wavelength of the light, usually expressed as some fraction of a meter, but it is sometimes expressed as some unit directly proportional to the photon energy, such as wave number or electron volts, which has a reciprocal relationship to wavelength.

Molecular electronic transitions take place when valence electrons in a molecule are excited from one energy level to a higher energy level. The energy change associated with this transition provides information on the structure of a molecule and determines many molecular properties such as color. The relationship between the energy involved in the electronic transition and the frequency of radiation is given by Planek's law. The electronic transitions of molecules in solution can depend strongly on the type of solvent with additional bathochromie shifts or hypsochromic shifts.

The instrument used in UV spectroscopy is called a UV spectrophotometer. To obtain absorption information, a sample is placed in the spectrophotometer and ultraviolet at a certain wavelength (or range of wavelengths) is shined through the sample. The spectrophotometer measures how much of the light is absorbed by the sample. The intensity of light before going into a certain sample is symbolized by $I_0$. The intensity of light remaining after it has gone through the sample is symbolized by I. The fraction of light transmittance is $(I/I_0)$, which is usually expressed as a percent Transmittance (% T). From this information, the absorbance of the sample is determined for that wavelength or as a function for a range of wavelengths. Sophisticated UV spectrophotometers can perform automatically. However, such UV spectrophotometers have very complicated structures, very costly, and usually bulky (not portable), for example, DU® Series 500 UV/Vis Spectrophotometer by Beckman Coulter, Inc. (Fullerton, Calif.).

Although the samples could be liquid or gaseous. A transparent cell, often called a cuvette, is used to hold a liquid sample in the spectrophotometer. The pathlength L through the sample is then the width of the cell through which the light passes through. Simple (economic) spectrophotometers may use cuvettes shaped like cylindrical test tubes, but more sophisticated ones use rectangular cuvettes, commonly 1 cm in width. For just visible spectroscopy, ordinary glass cuvettes may be used, but ultraviolet spectroscopy requires special cuvettes made of a UV-transparent material such as quartz.

UV absorption spectroscopy was never applied to directly measure/monitor quats concentration in a sanitizer solution.

SUMMARY OF THE INVENTION

It is an object of the present invention to measure the actual concentration of chemicals in a antimicrobial, cleaning, lubricating or pesticide solution.

It is another object of the present invention to measure an actual concentration of antimicrobial, surface active agent, lubricant or pesticide agent in a sanitizing solution.

It is further object of the present invention to measure an actual concentration of a detergent and an antimicrobial agent in a solution.

It is also an object of the present invention to provide a device to conduct the above-mentioned measurement directly, automatically, economically, continuously, and with a high sensitivity.

Other objects and advantages of the present invention may be seen from the following detailed description.

BRIEF DESCRIPTION OF THE DRAWINGS

The foregoing and additional features and characteristics of the present invention will become more apparent from the following detailed description considered with reference to the accompanying drawings in which like reference numerals designate like elements and wherein.

DETAILED DESCRIPTION OF THE INVENTION

To directly measure/monitor the concentration of quats automatically, continuously, and with a high sensitivity, the invention uses a spectrometer to measure absorbance properties of quats over the near UV (380-200 nm wavelength). Ultraviolet (UV) radiation is subdivided into near UV (380-200 nm wavelength) and extreme or vacuum UV (200-10 nm). When considering the effects of UV radiation on human health and the environment, the range of UV wavelengths is often subdivided into UVA (380-315 nm), also called Long Wave or "blacklight"; UVB (315-280 nm), also called Medium Wave; and UVC (<280 nm), also called Short Wave or "germicidal". The designs of the near UV spectrometer of the invention enable measuring the unique/ signature near UV spectrum of an macular of interest, such as quats.

Figure 1:
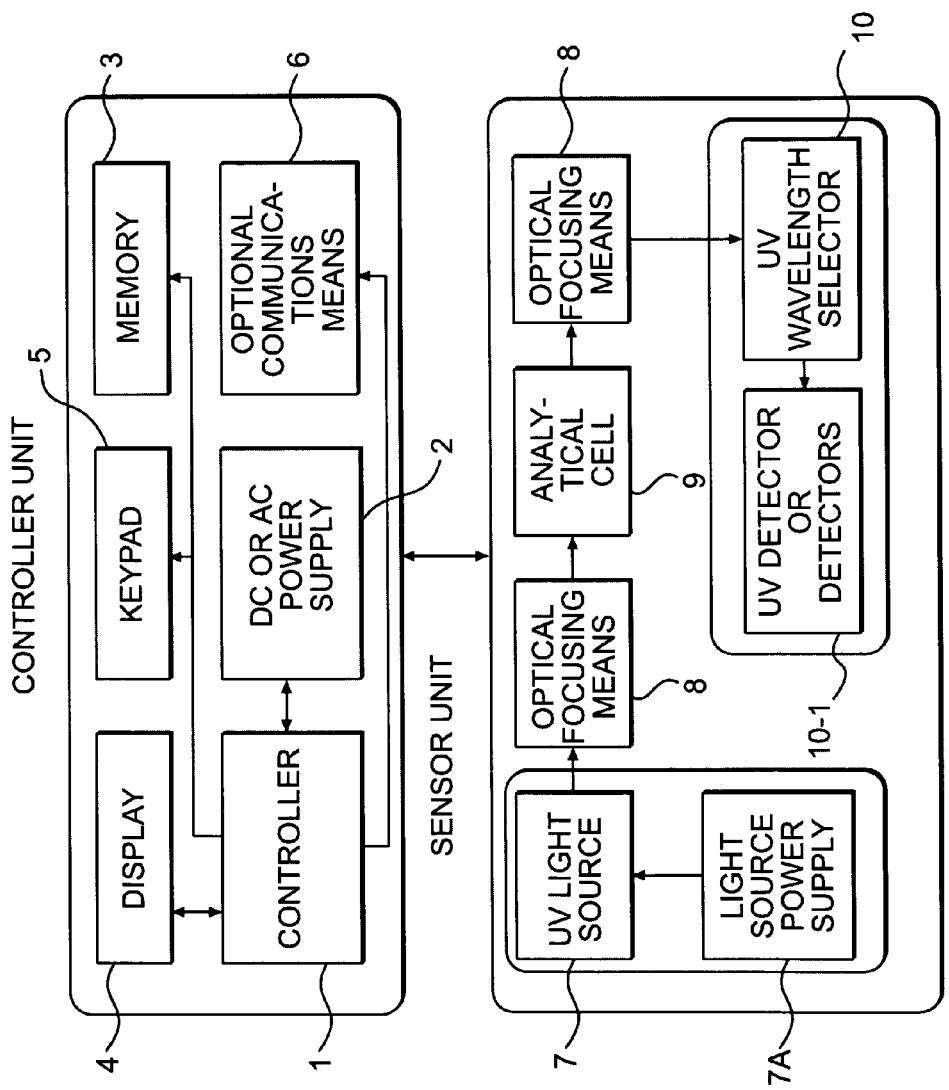
FIG. 1 shows a block diagram of an embodiment of a ultraviolet spectrometer of the invention.

FIG. 1 shows a block diagram of an embodiment of a ultraviolet spectrometer of the invention. The ultraviolet spectrometer 1000 (dimensions of 60 mm×35 mm×180 mm) has a controller 1, and a sensor unit including an ultraviolet light source 7 with a lamp power supply 7A, an analytical cell 9, an UV wavelength selector 10. The ultraviolet light source 7 emits light through a cell with solution, e.g., a sanitizing solution, for testing. The ultraviolet light source 7 may be a gas discharge lamp, such as a mercury lamp, a deuterium lamp, a metal vapor lamp, or a single or plurality of light emission diodes emitting light in a wavelength range of 200 nm to 320 nm. Preferably, the ultraviolet light source 7 may be a mercury low pressure lamp with main line at about 254 nm (model SCD70-9025-01 by BHK. Inc, Claremont Calif.) or a UV lamp such as a Krypton gas discharge lamp (Part No. 002405-002 by Hile Controls in Florida)). A light emission diode (model UV LED-255 from Photon Systems, Inc., Covina, Calif.) can be used as a light source. Optionally, an additional ultraviolet detector 7B is used to monitor intensity of the ultraviolet light source 7.

The analytical cell 9 can be a sample cell, a flow cell or an open path cell. The ultraviolet (UV) selector 10 has a UV array detector 10-1 and optical focusing means 8 which includes a ruled or holographic diffractional grating, or a variable wavelength linear interference filter or several interference filters. The controller 1 is included in a controller unit which transforms output signals from the UV array detector 10-1 into absorbance values or optical densities for two or more wavelengths in the range of 200 nm to 320 nm. The actual concentration of antimicrobial agent or detergent in a sanitizing solution is found by calculating difference in absorbance values for two or more wavelengths from about 230 nm to about 320 nm. The controller unit further includes a power supply 2, a memory 3, a display 4, a keypad 5, and an optional communication means 6. The power supply 2 may be a battery, a direct current (DC) from wall transformer or alternative current, e.g., 9V, 400 mA. The UV array detector 10-1 may includes UV photodiodes, UV photomultipliers, a CCD array, or a photodiode array.

Figure 2:
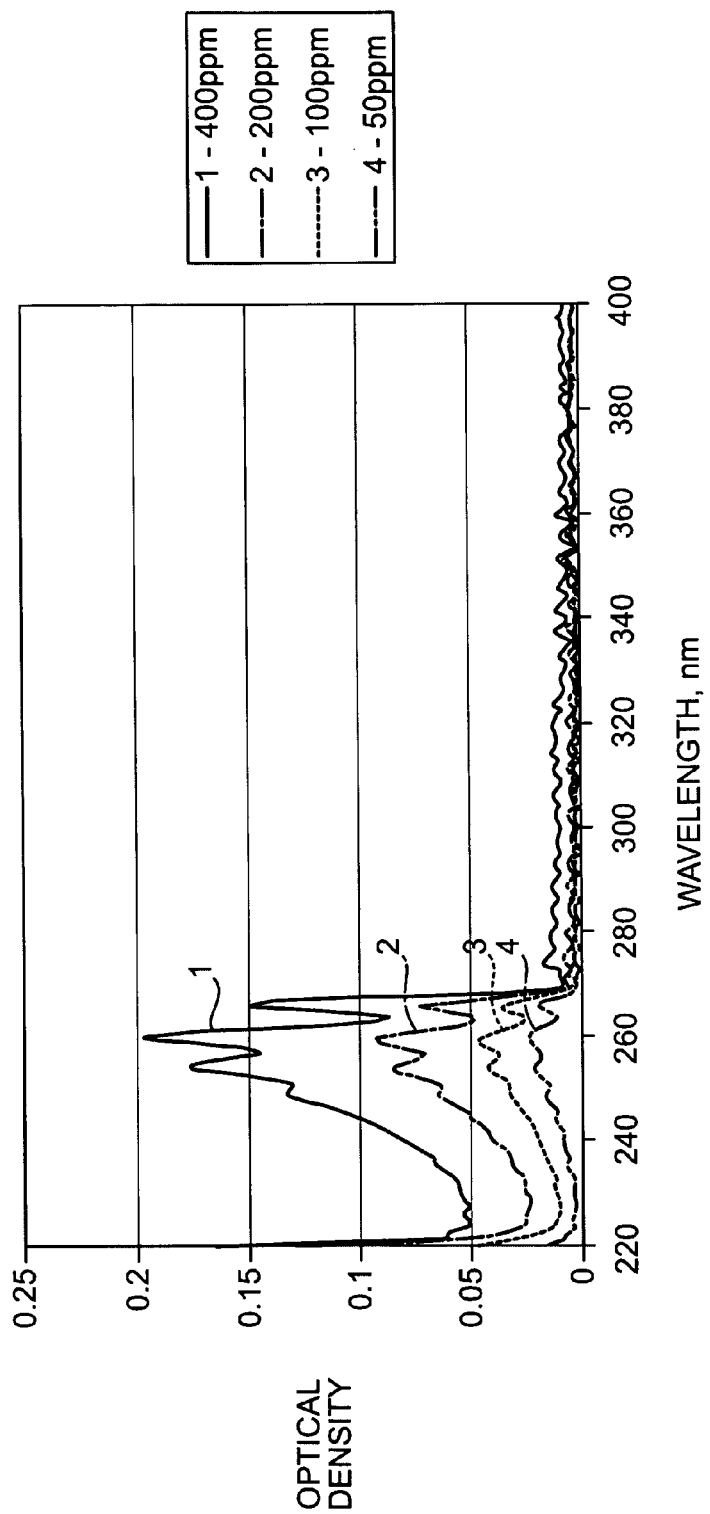
FIG. 2 shows an example of absorption spectra for a sanitizing solution (with zero contamination of detergents).
Figure 3:
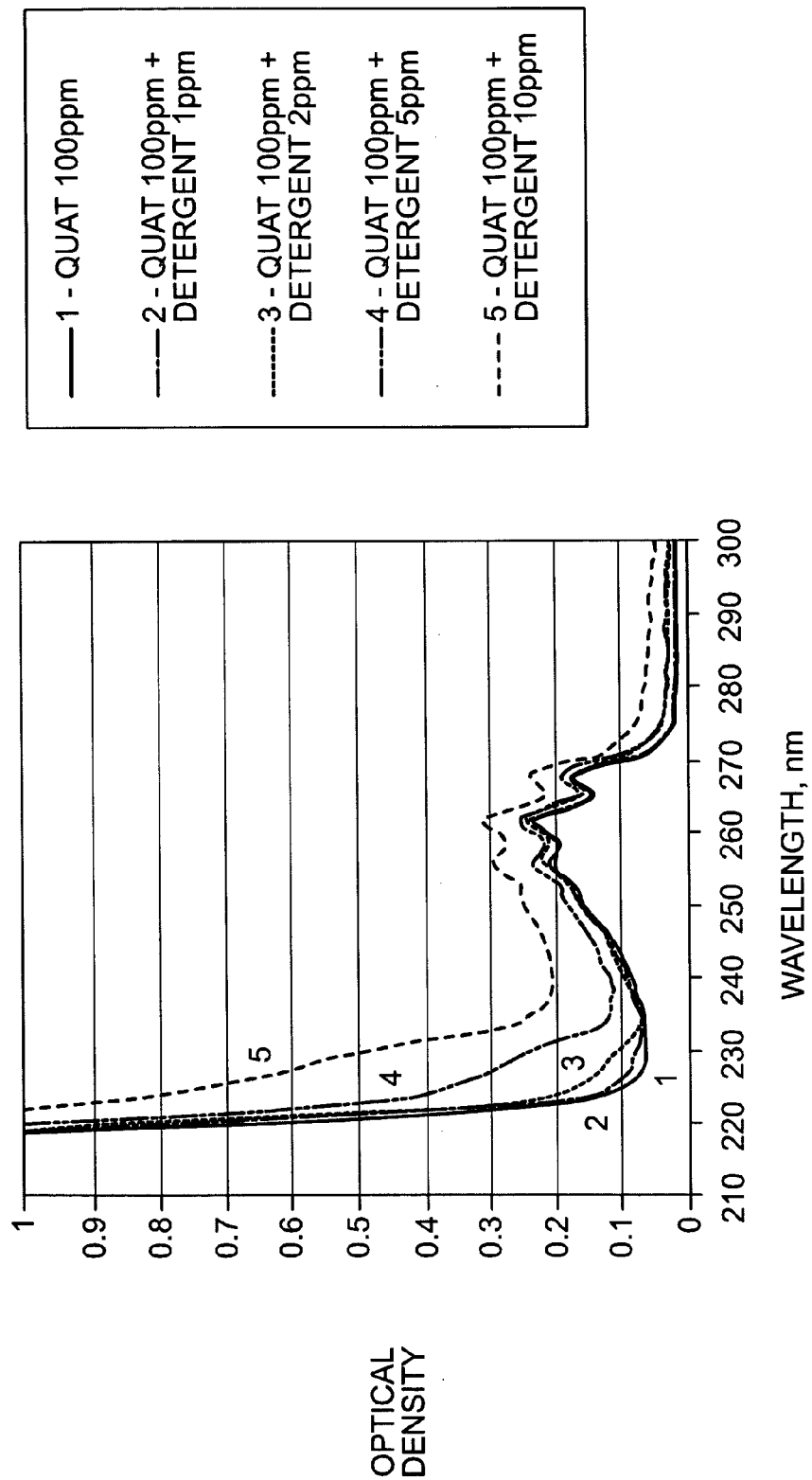
FIG. 3 shows spectral variations (shift of minimum position at 230 nm wavelength) in absorption for the same concentration of the sanitizing solution with different concentrations of a detergent.

FIG. 2 shows an example of absorption spectra for an OASIS 146 MULTI-QUAT SANITIZER® by Ecolab Inc. (St. Paul, Minn.) of concentrations from 50 ppm to 400 ppm in a solution (with zero contamination of detergents). OASIS 146 is a mixture of alkyl dimethyl benzyl ammonium chloride and dialkyl dimethyl ammonium chloride. The alkyl units refer to carbon chains ranging from approximately 8 to 20 carbon units. The Oasis 146 quat is used against, for example, *Pseudomonas aeruginosa, Staphylococcus aureus* and *Salmonella choleraesuis*. FIG. 3 shows spectral variations (shift of minimum position at 230 nm wavelength) in absorption for the same concentration 100 ppm of the OASIS 146 MULTI-QUAT SANITIZER® with different concentrations of a Pan Max Ultra Liquid Dish Detergent #19270 by Ecolab Inc.

Figure 4:
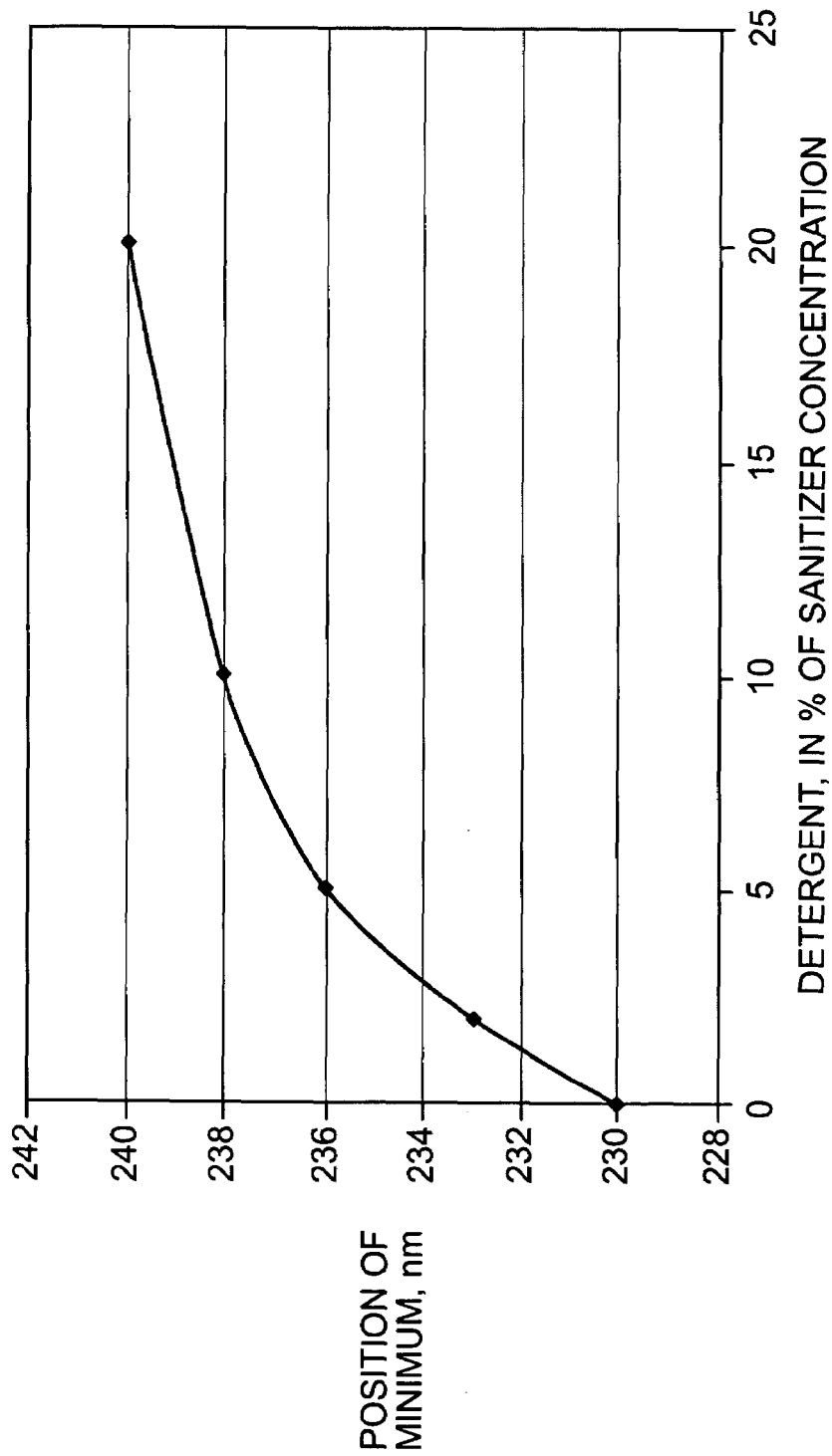
FIG. 4 shows where the percents of the detergent in the sample found using positions of a minimum in absorption in the range from 220 nm to 245 nm.

FIG. 4 shows where the percents of the detergent in the sample found using positions of a minimum in absorption in the range from 220 nm to 245 nm. The mathematic formula for the calibration curve in FIG. 4 is as follows:

$$y = 178.16 \cdot x - 14.608 \cdot x^2 + 0.5726 \cdot x^3 - 0.0081 \cdot x^4$$

where $y = \dfrac{\text{Concentration of detergent, } ppm}{\text{Concentration of sanitizer, } ppm}$ $x = $ (Position of minimum, nm $-$ 230 nm)

The % on the FIG. 4 is a ratio of detergent to sanitizer shown in %, rather than a % of concentration. For example, 1 ppm of the detergent and 100 ppm of the sanitizer will get 1% as the ratio. As another example, 2 ppm of the detergent and 200 ppm of the sanitizer will get the same 1% as the ratio and the same position of a minimum absorption.

The invention measures the actual concentration of chemicals in antimicrobial, cleaning, lubricating or pesticide solution with a method including steps of: (1) providing an ultraviolet spectrometer with a sample chamber, wherein the ultraviolet spectrometer comprises an ultraviolet light source emitting light having wavelengths of from about 200 nm to about 320 nm passing through a cell with sanitizing solution, a sample chamber, an ultraviolet dispersive system with a detector, a controller to transform output signals from the UV detector into absorbance values or optical density for two or more wavelengths from about 200 nm to about 320 nm; (2) providing a liquid or gaseous medium containing chemicals wherein the chemicals are one or more agents to produce a desired antimicrobial, cleaning, pesticidal, or lubricating action; (3) using the ultraviolet spectrometer to measure the absorbance spectrum for two or more wavelengths from about 200 nm to about 320 nm; (4) programming the controller to calculate the difference in absorbance value i.e., optical density for two or more wavelengths from about 200 nm to about 320 nm; (5) determining the actual concentration of antimicrobial, surface active, pesticide or lubricating agents in a solution using the calculated difference in absorbance values for two or more wavelengths from about 200 nm to about 320 nm and the calibration constants found for a known concentrations of the agents. For example, when using a mercury lamp, sample concentrations $C_{quat}$ can be evaluated based upon the follow equations:

$$C_{quat} = 2852 \cdot Z(s) \cdot (1 - 0.042 \cdot Z(s)^2)$$

$$Z(s) = (D_{254}(s) - 2.62 \cdot D_{280}(s) + 1.62 \cdot D_{296}(s))$$

$$D_{254}(s) = \log\left(\frac{U_{254}(0)}{U_{254}(s)}\right)$$

is an optical density at the wavelength 254 nm $$D_{280}(s) = \log\left(\frac{U_{280}(0)}{U_{280}(s)}\right)$$

is an optical density at the wavelength 280 nm $$D_{296}(s) = \log\left(\frac{U_{296}(0)}{U_{296}(S)}\right)$$

is an optical density at the wavelength 296 nm $U_{254}$ (0), $U_{280}$ (0) and $U_{296}$ (0) are intensities of ultraviolet signals at wavelengths of 254 nm, 280 nm and 296 nm during zeroing, and $U_{254}$(s), $U_{280}$(s) and $U_{296}$(s) are intensities of ultraviolet signals at wavelengths 254 nm, 280 nm and 296 nm during measuring the sample solution, For krypton lamp or deuterium lamp the optimal equation shown below $$C_{quat} = 2450 \cdot (D_{259}(s) - D_{275}(s))$$

Where $C_{quat}$ is the actual concentration of chemicals, $$D_{259}(S) = \log\left(\frac{U_{259}(0)}{U_{259}(s)}\right)$$

is an optical density at the wavelength 259 nm, $$D_{275}(S) = \log\left(\frac{U_{275}(0)}{U_{275}(s)}\right)$$

is an optical density at the wavelength 275 nm, $U_{259}$ (0) and $U_{275}$ (0)—intensity of ultraviolet signals at wavelengths 259 nm and 275 nm during zeroing, $U_{259}$ (s) and $U_{275}$(s)— intensity of ultraviolet signals at wavelengths 259 nm and 275 nm during measuring the sample solution. Another set of wavelengths, for example, 260 nm and 264 nm, can be used in some embodiments. Two or three wavelength equations are shown for illustration only. Embodiments with a krypton lamp, a deuterium lamp or another broad band UV light source can use for absorbance data in an UV range from approximate 220 nm to approximate 320 nm. Absorbance in the range from 220 nm to 270 nm shows specific peaks in QUAT absorbance (FIG. 2), and the range from approximate 270 nm to approximate 320 nm allows to evaluate a position of a background line for subtracting a background evaluated value from the measurement results so as to eliminate influence of turbidity or other components from the QUAT measurements.

Figure 5:
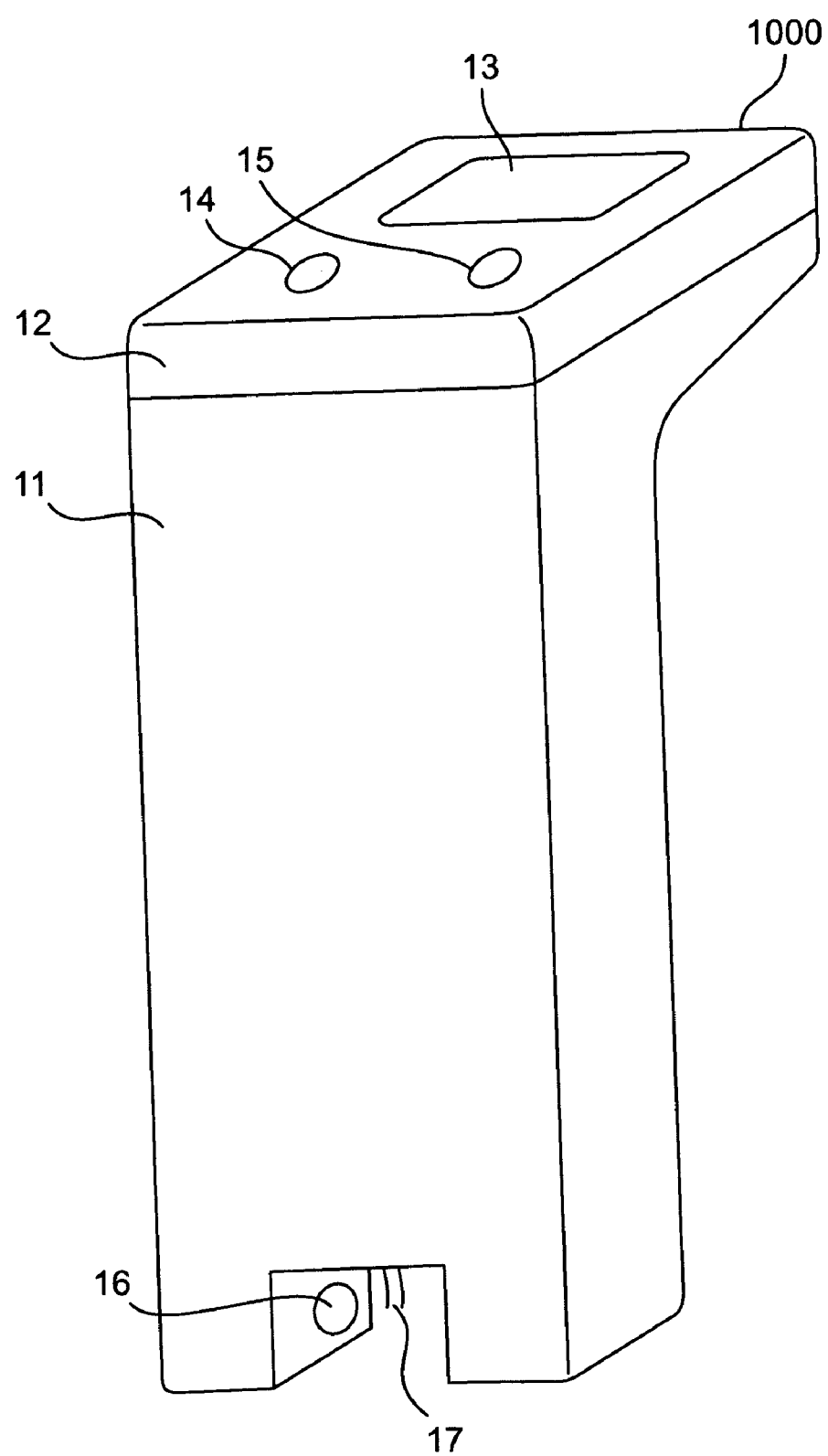
FIG. 5 shows a perspective view of a first embodiment of a handheld ultraviolet spectrometer of the invention.

FIG. 5 shows a perspective view of a first embodiment of a handheld ultraviolet spectrometer 1000 of the invention. The ultraviolet spectrometer 1000 includes a housing 11, a lid 12 with a display 13 which shows the spectrometer status, the result of the last measurement and the currently chosen calibration, a "START" button 14, a "ZERO" button 15, an output window 16 for UV beam, and an analytical area 17. The "START" button 14 is pressed for each new pressing to take a new measurement. Pressing and holding the "START" button 14 turns the ultraviolet spectrometer 1000 OFF. The "ZERO" button 15 is pressed for changing calibration The ultraviolet spectrometer 1000 has several variants of calibration in memory, each of which includes measuring UV absorbance for a specific product containing QUAT. For example, two products Oasis 144 and Oasis 146 have different compositions and different concentrations of components. The ultraviolet spectrometer 1000 can be programmed to measure UV signals at 260 nm and 264 nm and use the same equation to calculate a concentration.

$$C_{quat} = A_i \cdot \left(\log\left(\frac{U_{260}(s)}{U_{260}(0)}\right) - \log\left(\frac{U_{264}(s)}{U_{264}(0)}\right)\right),$$

where $U_{260}$ (s), $U_{264}$ (s) are UV signals during measuring, and $U_{260}$ (O), $U_{264}$ (O) are UV signals during zeroing. $A_i$ is a calibration constant stored in the memory. $A_i = A_{144} = 1794$ for Oasis 144, and $A_i = A_{146} = 4500$ Oasis 146. Pressing and holding the "ZERO" button 15 initiates the ultraviolet spectrometer 1000 zeroing. For zeroing, the ultraviolet spectrometer 1000 should be inserted in water to measure and then save in memory initial levels of intensity of ultraviolet signals for all wavelengths in a designed spectrometer range.

Figure 6:
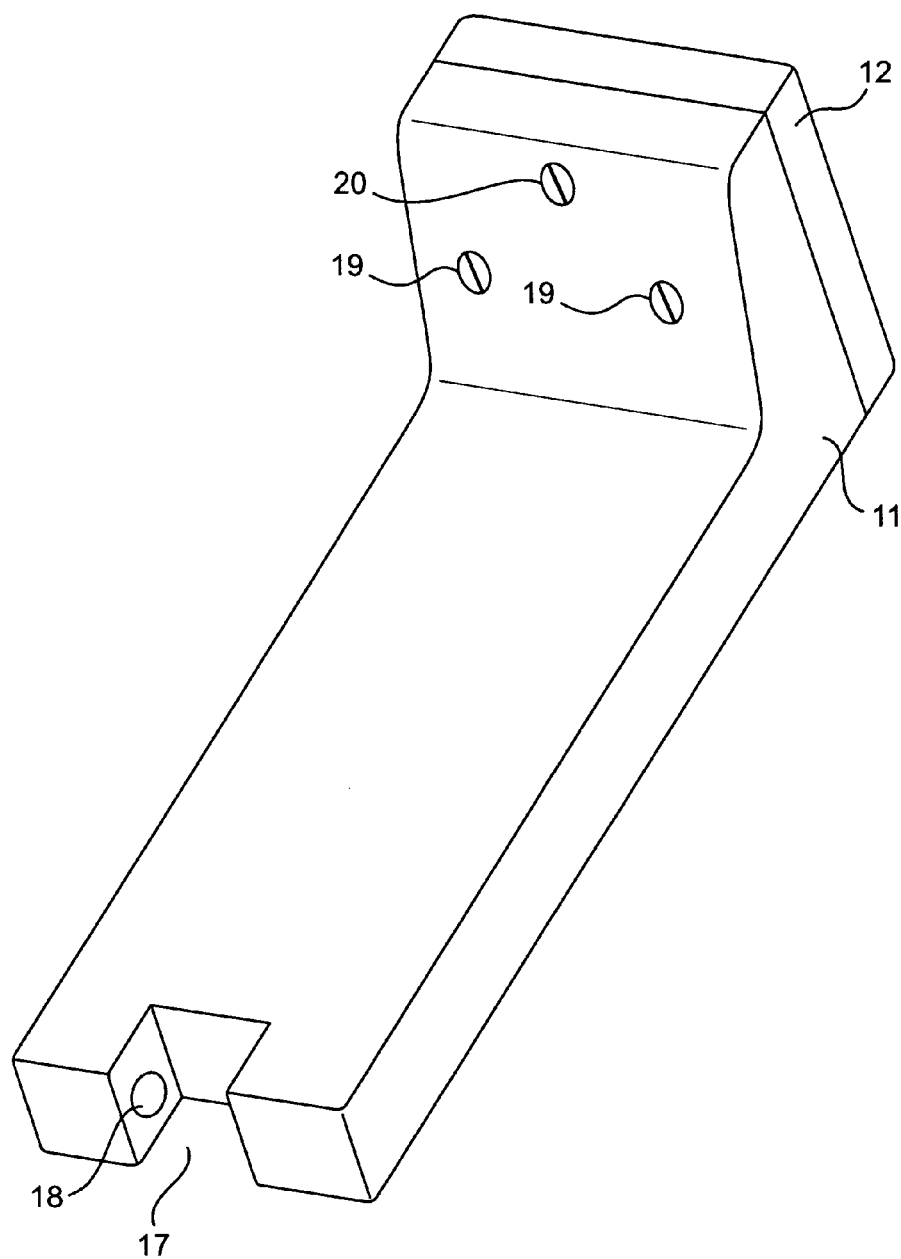
FIG. 6 shows another perspective view the ultraviolet spectrometer of the invention.

FIG. 6 shows another perspective view the ultraviolet spectrometer 1000 of the invention, which shows an input window 18 for UV beam for receiving the UV beam from the output window 16 across the analytical area 17, service screws 19 for a battery replacement procedure, and security screw 20 for a lid release procedure during factory calibration.

Figure 7:
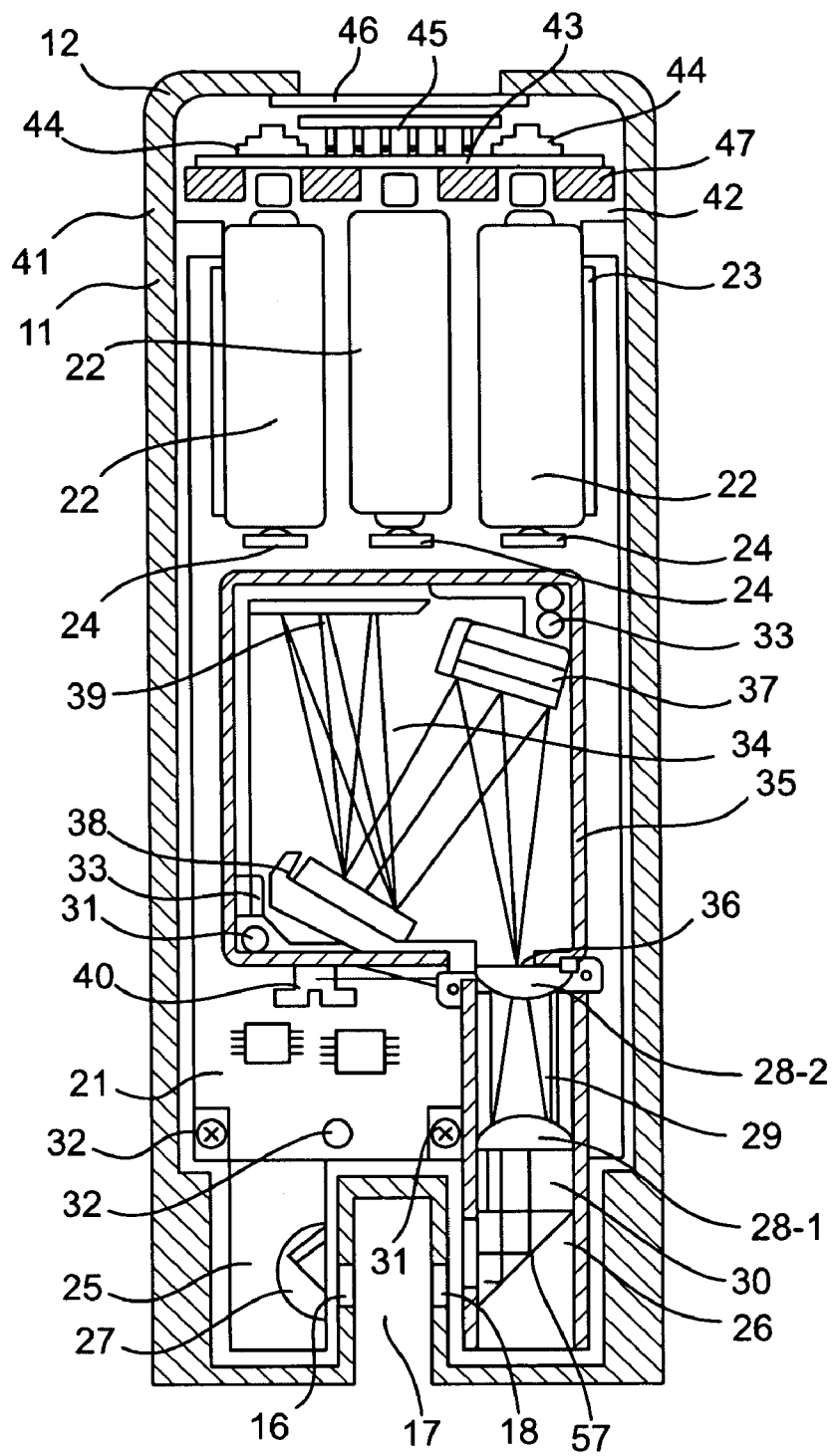
FIG. 7 shows a cross-section view of the ultraviolet spectrometer of the invention.
Figure 8:
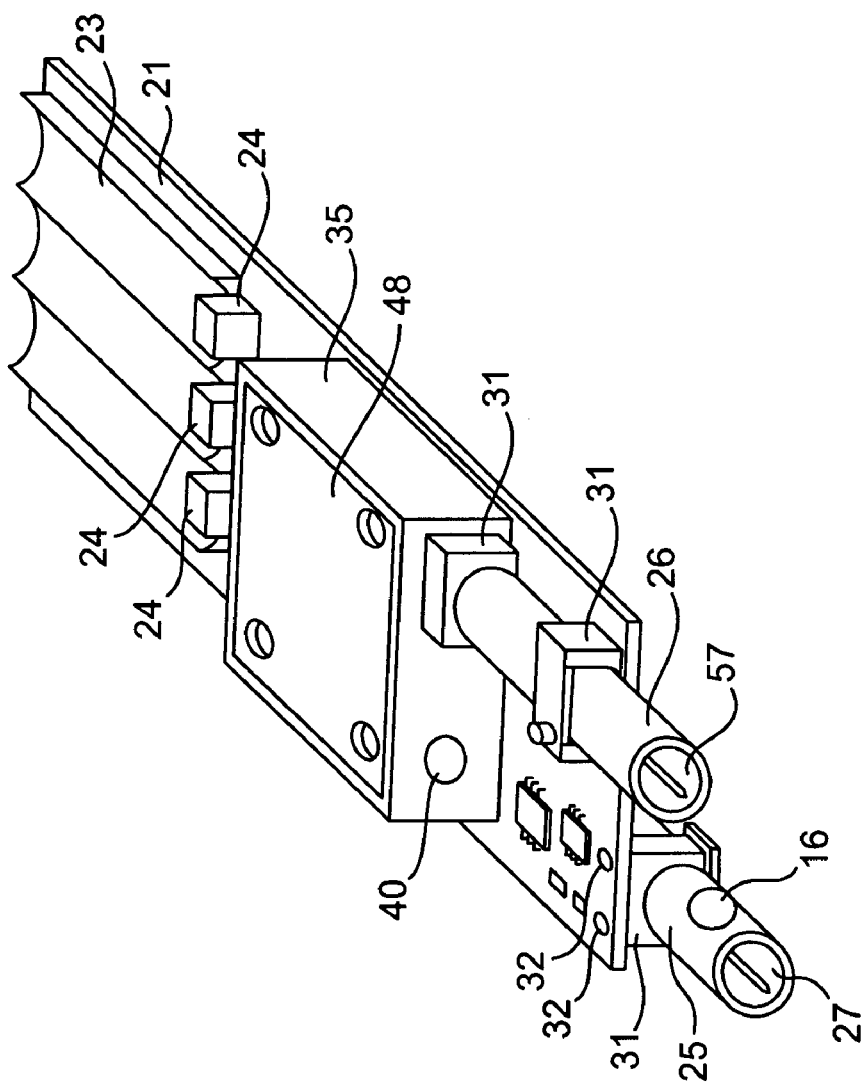
FIG. 8 shows a second cylinder side of a printed board in the ultraviolet spectrometer of the invention.
Figure 9:
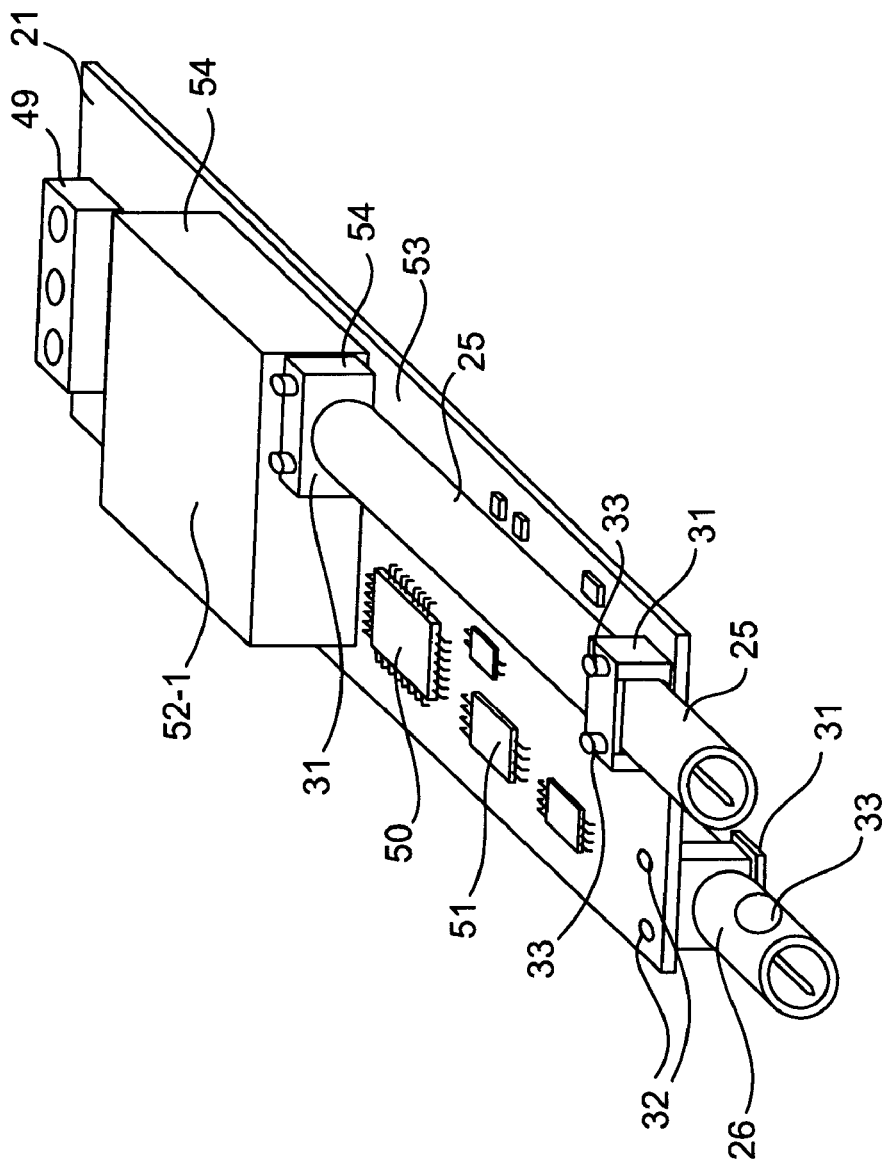
FIG. 9 shows a first cylinder side of the printed board in the ultraviolet spectrometer of the invention.

FIG. 7 shows a cross-section view of the ultraviolet spectrometer 1000 of the invention. Within the housing 11, there are a printed board 21, three AA batteries 22, a battery support 23, battery contacts 24 soldered into the printed board 21, a first cylinder 25, a second cylinder 26, and a UV wavelength selector 34. FIG. 8 shows the second cylinder side of the printed board 21, and FIG. 9 shows the first cylinder side of the printed board 21.

The first cylinder 25 accommodates a first prismatic mirror 27 and the UV source 7. The first prismatic mirror 27 has a cylindrical shape with two end faces. At one side, the end face is normal to the cylinder axis. Another end face (hypotenuse side) is tilted for 45 degrees. It is polished and coated with aluminum. The first prismatic mirror 27 has its hypotenuse side face up. The first cylinder 25 is shielded from a power supply 52 for supplying power to the light source 7 via a grounding wire 53 connecting the first cylinder 25 to the shield 54 which is soldered for grounding at places 54. The power supply 52 (FIG. 10) is accommodated in a metal shield 52-1 (FIG. 9) to supply power to the light source 7. FIG. 9 also shows a display connector 49 for connecting the display 13 to the printed board 21, a controller chip 50 and a memory chip 51 both soldered to the printed board 21. As shown in FIGS. 8-9, the first cylinder 25 fits into a pair of cylinder holders 31 which are mounted to the printed board 21 with cylinder holder screws 32. The threaded holes 33 are provided for mounting the screws 32 to the printed board 21.

The second cylinder 26 accommodates a second prismatic mirror 57 (shaped identical with the first prismatic mirror 27), lenses 28-1, 28-2, a first spacer 29 (a cylinder tube with an outside diameter of 8 mm, an inside diameter of 7 mm and a length of 18 mm), and a second spacer 30 (a cylinder tube with an outside diameter of 8 mm, an inside diameter of 7 and a length of 5 mm), The lenses 28-1, the first spacer 29, the lenses 28-2, and the second spacer 30 are aligned along an axis of the second cylinder 26 in order. As shown in FIGS. 8-9, the second cylinder 26 fits into another pair of cylinder holders 31 which are also mounted to the printed board 21 with other cylinder holder screws 32. The second cylinder 26 is connected to a spectrometer frame 35 with a spectrometer cover 48 covering thereon and a wavelength adjustment screw 40. FIG. 8 also shows the battery support 23, three battery contacts 24 for connecting the batteries 22 with the printed board 21.

The UV wavelength selector 34 includes an input slit 36, a spherical mirror 37 (dimensions of 14 mm×14 mm), a diffraction gratings 38 (dimensions of 12.7 mm×12.7 mm, model NT43-750 made by Edmund Optics, Inc., Barrington, N.J.) and a detector array 39 (including 128 elements, dimensions of 10.3 mm×15.3 mm model MLX90255-BAR. made by Melexis Microelectronics System, Concord, N.H.). The input slit 36 is also symmetrically aligned with the axis of the second cylinder 26. A receiving surface of the detector array 39 is positioned perpendicular to the axis of the second cylinder 26. The center of the spherical mirror 37 is aligned with the axis of the second cylinder 26, while its bottom is positioned at a 20 degree angle from the axis of the second cylinder 26. The center of the diffraction gratings 38 corresponds to the center of the spherical mirror 37 such that the diffraction gratings 38 reflects UV lights of different wavelengths under different angles to produce a linear spectrum on the detector array 39. The center of the detector array 39 corresponds to the center of the diffraction gratings 38 so as to position UV wavelengths from 220 nm to 360 nm on the detector array 39. A UV light emits from the light source 58, focused by the lens 28-3, reflected by first prismatic mirror 27, then passes via the output window 16, the analytical area 17, the input window 18, then reflected by the second prismatic mirror 57 to pass via the first spacer 30, the lenses 28-1, the second spacer 29, the lenses 28-2, and then into the UV wavelength selector 34. Inside the UV wavelength selector 34, the UV light passes via the input slit 36 of 2-5 mm long and 0.05 mm wide, then reflected by the spherical mirror 37 to the diffraction gratings 38 to be diffracted towards the detector array 39. By adjusting the adjustment screw 40 from outside, the angle position of the diffraction gratings 38 is changed. Small rotation of the diffraction gratings 38 changes positions of UV wavelengths on the detector array 39 thus affecting the reading by the detector array 39. The lenses 28-1 and the lenses 28-2 shape differently. The lens 28-1 produces the image of the light source on the input slit 26, and the lens 28-2 produces image of the lens 28-1 on the mirror 37.

FIG. 7 also shows a rubber gasket 41 of the lid 12 smugly fits with a cover plate 42 of the housing 11 to ensure proper contacts between the batteries and the contact spring in the lid 12. The display 13 includes a display board 43, three battery spring contacts 61, two push-buttons 44 (for receiving the pressure from the "START" button 14 and the "ZERO" button 15 respectively), an LCD screen 45, a display window 46, and a protection plate 47.

Figure 10A:
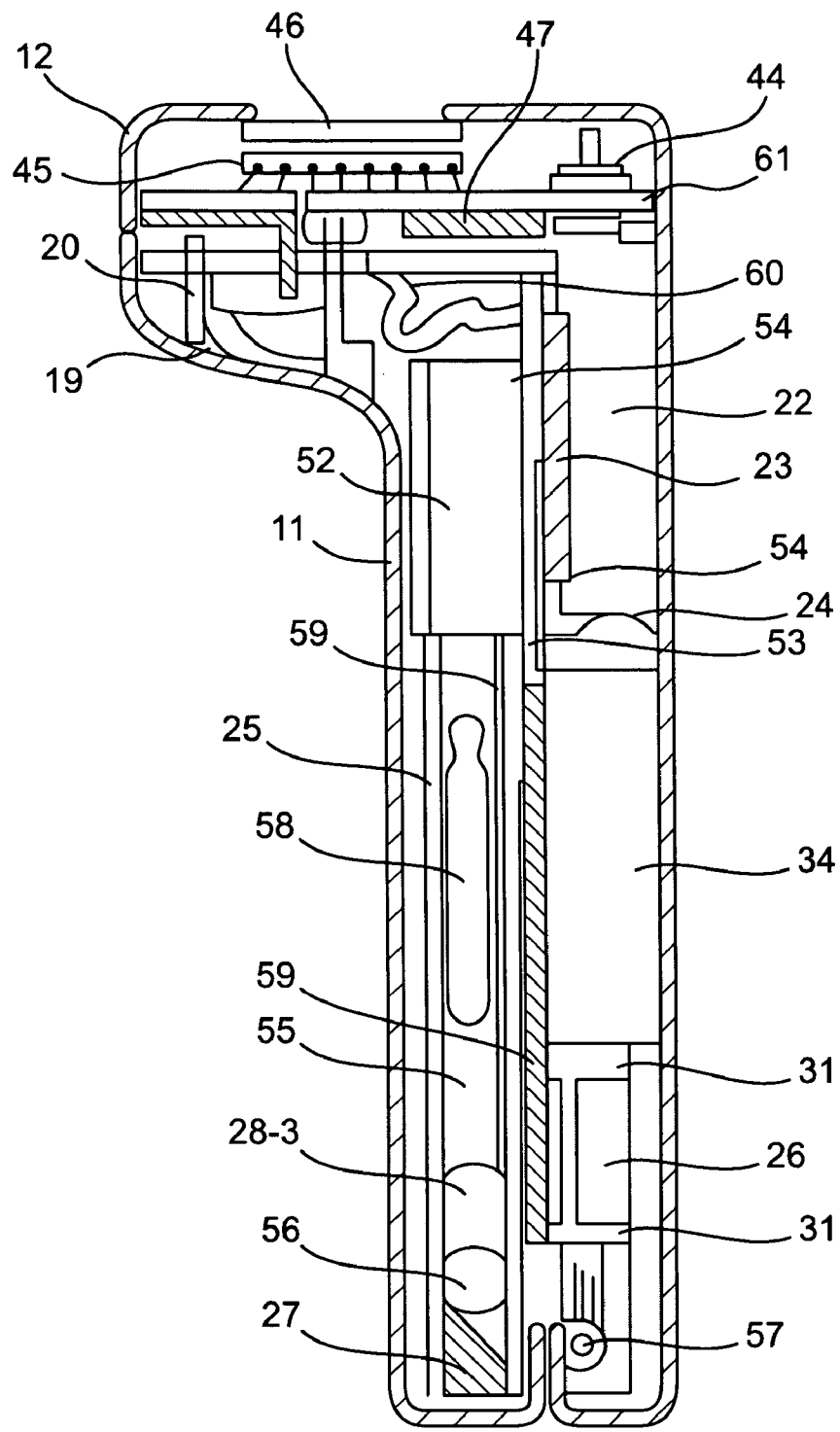
FIGS. 10A-B show another cross-sectional view of the ultraviolet spectrometer of the invention with a UV lamp and a UV LED respectively.

FIG. 10A shows another cross-sectional view of the ultraviolet spectrometer 1000 of the invention. FIG. 10A also shows the service screws 19 for a battery change procedure, the security screw 20 for releasing the lid 12 during factory calibration, a lens 28-3 for collecting light from the UV lamp 58 and focusing it in the analytical area 17, a third spacer 55 (a cylinder tube with a diameter of 8 mm and a length of 18 mm), a forth spacer 56 (a cylinder tube with a diameter of 8 mm and a length of 13 mm), a UV lamp 58, mounting screws 59 for mounting the UV dispersive system 34 to the printed board 21, and a display cable 60. The UV lamp 58 can be a gas discharge UV mercury lamp, or a deuterium lamp (model no. DTM 6/10 by Heraeus Noblelight LLC, Duluth, Ga.), or a pulse xenon lamp.

Figure 10B:
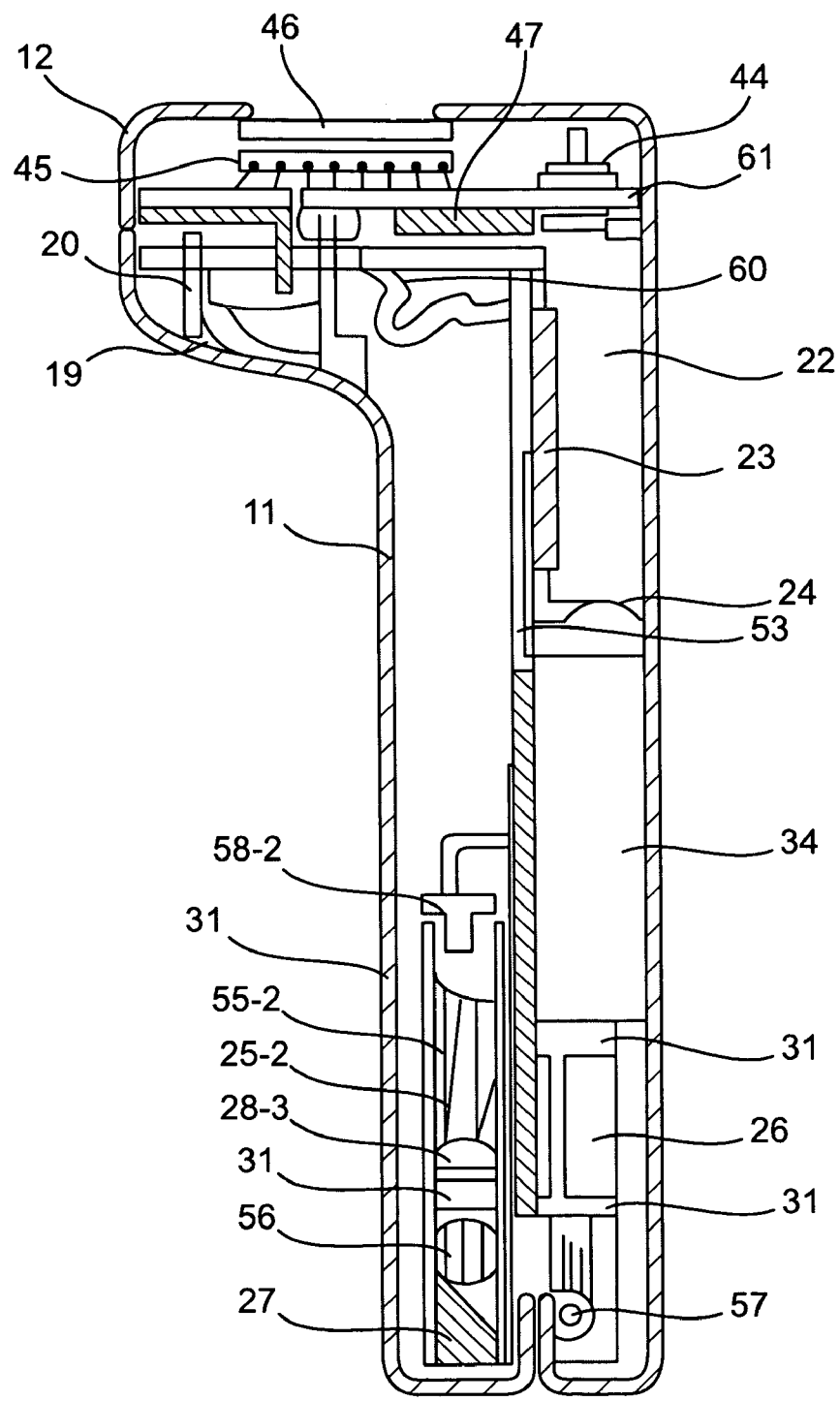

FIG. 10B shows a cross-sectional view of another embodiment of the ultraviolet spectrometer 1000 of the invention. Instead of the shielded power supply 52 and the UV lamp 58, a UV LED-255 is used. It is placed in a third spacer 25-2 which is secured inside of the first cylinder 55-2. The UV LED works only 5-10 seconds during each measurement and then it is turned off to increase its life time. As an UV light source, the UV LED is more convenient than a gas discharge UV mercury lamp, since it works with low voltages, consumes less than 0.2 Watts and allows high frequency modulation which improves a signal to noise ratio.

Figure 11C:
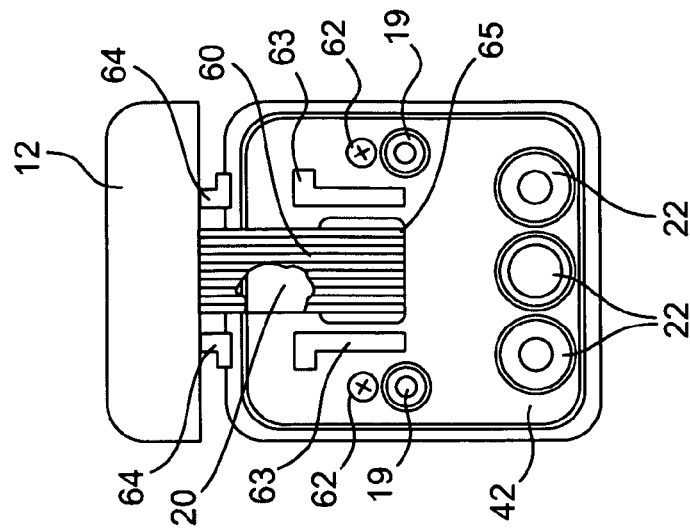
FIG. 11C shows the lid is slid away from a housing of the ultraviolet spectrometer.
Figure 11B:
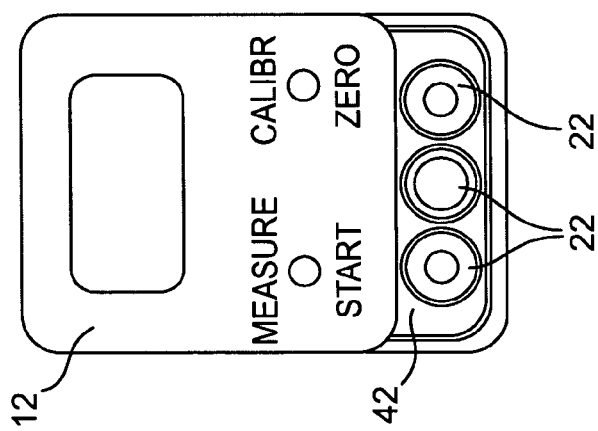
FIG. 11B show a lid is shifted to open for replacing batteries in the ultraviolet spectrometer.
Figure 11A:
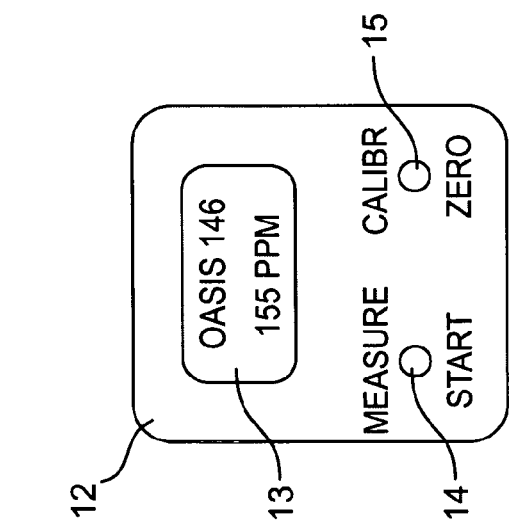
FIG. 11A shows a top view of the ultraviolet spectrometer of the invention.

FIG. 11A shows a top view of the ultraviolet spectrometer 1000 of the invention. The display 13 shows "Oasis 146 155 ppm". On the lid 12, "MEASURE" and "START" are printed on the up and down side of the "START" button 14, and "CALIBR" and "ZERO" are printed on the up and down side of the "ZERO" button 15. By releasing the service screws 19, a pair of protection plate locking members 64 inside the lid 12 can be slid along a corresponding pair of cover plate slide channels 63 on the cover plate 42 of the housing 11 such that the lid 12 can be shifted to open for replacing the batteries 22 as shown in FIG. 11B. By releasing the security screw 20, the protection plate locking members 64 inside the lid 12 can be slid out of the cover plate slide channels 63 on the cover plate 42 of the housing 11 such that the lid 12 can be totally relapsed from the housing 11 as shown in FIG. 11C. The security screw 20 is covered with a soft silicon compound after factory assembling to allow only authorized access for factory repairing. The display cable 60 remains connected during the lid release. FIG. 11C also shows a pair of cover plate screws 62 for securing the cover plate 42 to the housing 11, and an opening on the cover plate 42 for accommodating the display cable 60 there through.

Figure 12A:
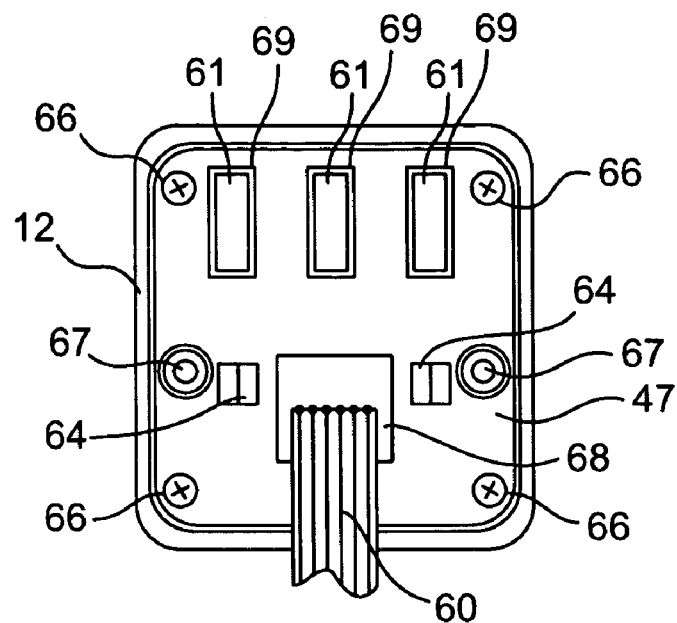
FIG. 12A shows the inside of the lid of the ultraviolet spectrometer.
Figure 12B:
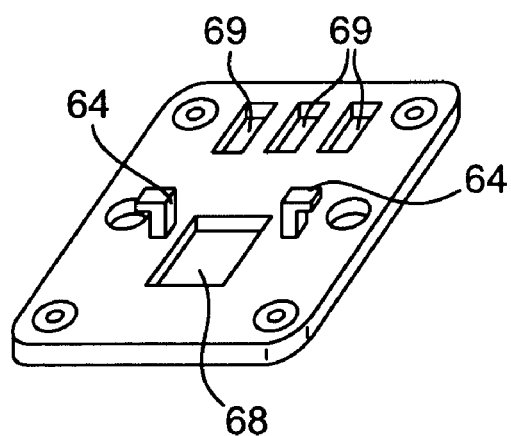
FIG. 12B shows a perspective view of a protection plate of the ultraviolet spectrometer.
Figure 12C:
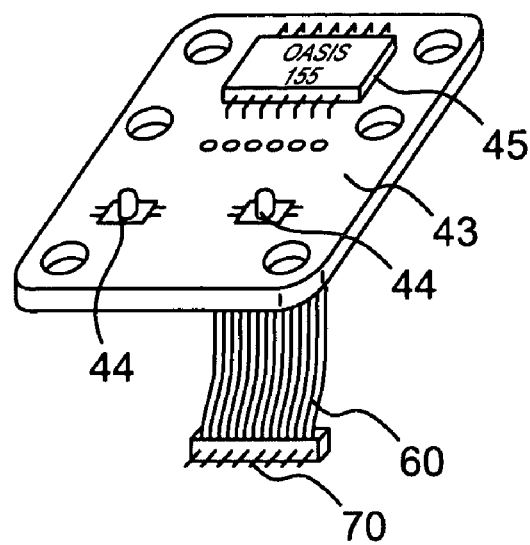
FIG. 12C shows a prospective view of a display board of the ultraviolet spectrometer.
Figure 12D:
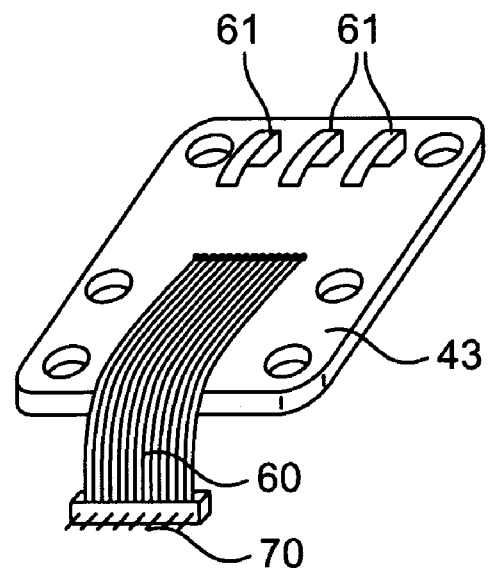
FIG. 12D shows the other side of the display board of the ultraviolet spectrometer.

FIG. 12A shows the inside of the lid 12 including the display cable 60, the battery spring contacts 61, the pair of protection plate locking members 64, mounting screws 66 for the protection plate 47, threaded holes 67 for the service screws 19, an opening 68 for the display cable 60, and openings 69 for the battery spring contacts 61. FIG. 12B shows a perspective view of the protection plate 47. FIG. 12C shows a prospective view of the display board 43 from the top including the display board 43, the momentary push-buttons 44, the LCD screen 45, the display cable 60, and a cable connector 70 to be connected to the connector 49 on the printed board 21 in FIG. 9. FIG. 12D shows the other side of the display board 43.

Figure 13A:
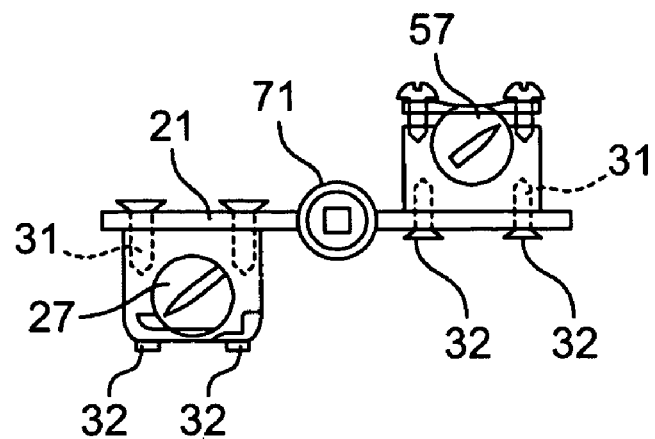
FIG. 13 shows a second embodiment of the handheld ultraviolet spectrometer of the invention
Figure 13B:
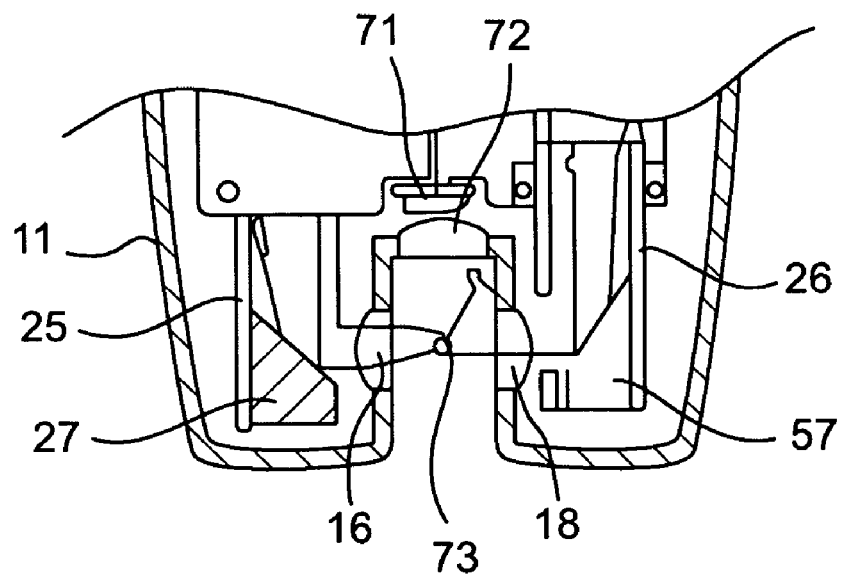

FIG. 13 shows a second embodiment of the handheld ultraviolet spectrometer 1000 of the invention, which has an additional detector for scattering measurements. FIGS. 13A-B shows a second UV detector 71 for scattering measurements which is positioned between the first cylinder 25 and the second cylinder 26 in side the housing 11. The UV detector 71 is placed over a third window 72 which is right on top of the analytical area 17, which lies between the output window 16 and the input window 18 on the UV transmission path, thereby receiving scattered radiation from the analytical area 17. The embodiment tests turbidity of the sample solution then compensates for turbidity influence on the sanitizer detecting result. The compensated concentration value Ccomp can be calculated from the following equation:

$$C_{comp} = C_{meas} - K_t \cdot U_t(s)$$

$C_{meas}$ is a not-compensated output concentration value. $U_t(s)$ is a turbidity channel output (amplified signal from the UV detector 71) during measuring of an unknown sample.

$$K_t = \frac{C_{meas}(T_{st})}{U_t(T_{st})}$$

is a compensation coefficient, where $C_{meas}$ ($T_{st}$) is a not-compensated output concentration value, and $U_t(T_{st})$ is an output of a turbidity channel during calibration when calibration solution has a turbidity of $T_{st}$ and zero concentration of sanitizer. Usually the turbidity of sanitizing solutions does not exceed 10 NTU. The compensation coefficient $K_t$ should be found individually for each spectrometer using a standard turbidity solution with turbidity from 1 NTU to 10 NTU.

The described embodiment allows compensating turbidity influence and also allows setting a trigger point when the sanitizing solution should be discarded due to excessive contamination and being associated high level of turbidity. There are two standard specifications for turbidity measurement that are generally adapted worldwide: the International Standard ISO 7027 (Water quality—Determination of Turbidity, International Standard, Third Edition, 1999-12-15) and the USEPA 180.1 (Nephelometric Method 2130 B, Standard Methods for the Examination of Water and Wastewater, 1989). Both methods measure the intensity of light scattered at 90° to the path of incident light. For Example, a method for testing turbidity is described U.S. Pat. No. 6,836,332, which is hereby incorporated by reference.

Figure 14:
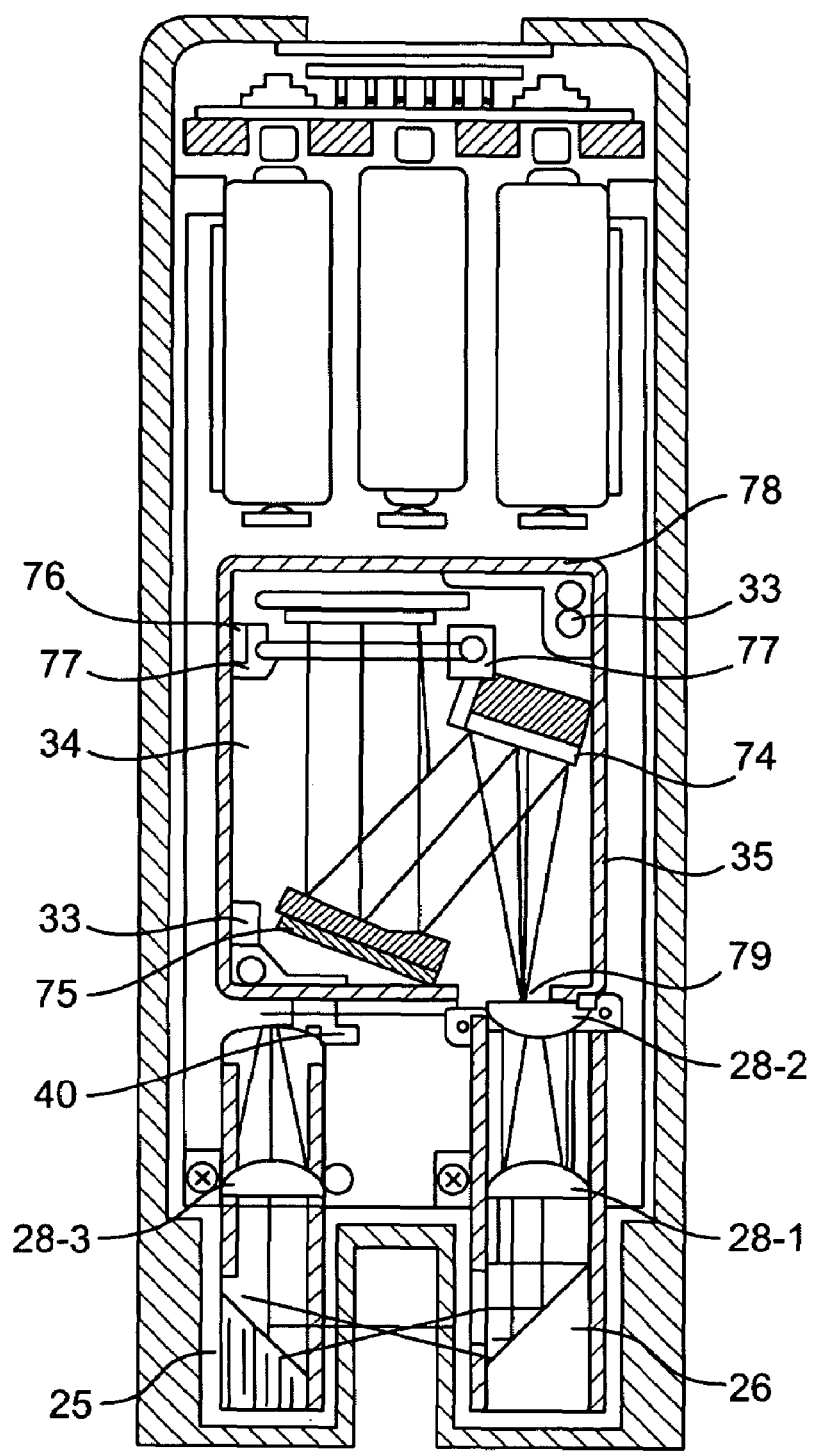
FIG. 14 shows a third embodiment of the handheld ultraviolet spectrometer of the invention which applies a variable wavelength UV filter in a UV separation system of the ultraviolet spectrometer.

FIG. 14 shows a third embodiment of the handheld ultraviolet spectrometer 1000 of the invention which applies a linear variable wavelength UV filter 76 (dimensions of 10 mm×50 mm, model no. LVF-UV-HL (230-500 nm) made by Ocean Optics, Inc., Dunedin, Fla.) in the UV separation system 34. This embodiment replaces the input slit 36, the spherical mirror 37, the diffraction gratings 38, and the detector array 39 in FIG. 7 with a flat mirror 74, an astigmatic mirror (toroidal mirror) 75, the variable wavelength optical UV filter 76, a pair of UV filter mounts 77, a linear detector array 78, and an input diaphragm 79. The two UV filter mounts 77 mount the variable wavelength optical UV filter 76 on the printed board 21. The input diaphragm 79 is symmetrically aligned with the axis of the second cylinder 26. A receiving surface of the linear detector array 78 is positioned perpendicular to the axis of the second cylinder 26. The center of the flat mirror 74 is aligned with the axis of the second cylinder 26, while its bottom is positioned at a 20-degree angle from the axis of the second cylinder 26. The center of the astigmatic/toroidal mirror 75 corresponds to the center of the flat mirror 74 such that the flat mirror 74 directs UV light from the input diaphragm 79 to the astigmatic (toroidal) mirror 75 which transforms light from a circular input diaphragm into the line on the sensitive surface of the linear detector array 78. The center of the linear detector array 78 corresponds to the center of the astigmatic/toroidal mirror 75 such that The UV light passes through the linear variable wavelength UV filter 76 and reaches the linear detector array 78. The variable wavelength optical UV filter 76 has a wavelength range from 230 nm to 320 nm and a bandpass near 20 nm.

A UV light emits from the light source 7, focused by the lens 28-3, reflected by first prismatic mirror 27, then passes via the output window 16, the analytical area 17, the input window 18, then reflected by the second prismatic mirror 57 to pass via the first spacer 30, the lenses 28-1, the second spacer 29, the lenses 28-2, and then into the UV wavelength selector 34 as in the embodiment shown in FIG. 7. Inside the UV wavelength selector 34, the UV light passes via the input diaphragm 79 with a diameter of opening 3 mm, then reflected by the flat mirror 74 (dimensions of 14 mm×14 mm) to the astigmatic/toroidal mirror 75 (doughnut-shaped with dimensions of 25 mm×14 mm, and a radius of curvature near 70 mm in the plane parallel to the printed board and a radius of curvature near 23 mm in a perpendicular plane) towards variable wavelength optical UV filter 76 and then the linear detector array 78 (identical to the detector array 39 in FIG. 7). By adjusting the adjustment screw 40 from outside, the position of the astigmatic/toroidal mirror 75 is changed thus affect focusing the UV light on the surface of the linear detector array 78.

Figure 15:
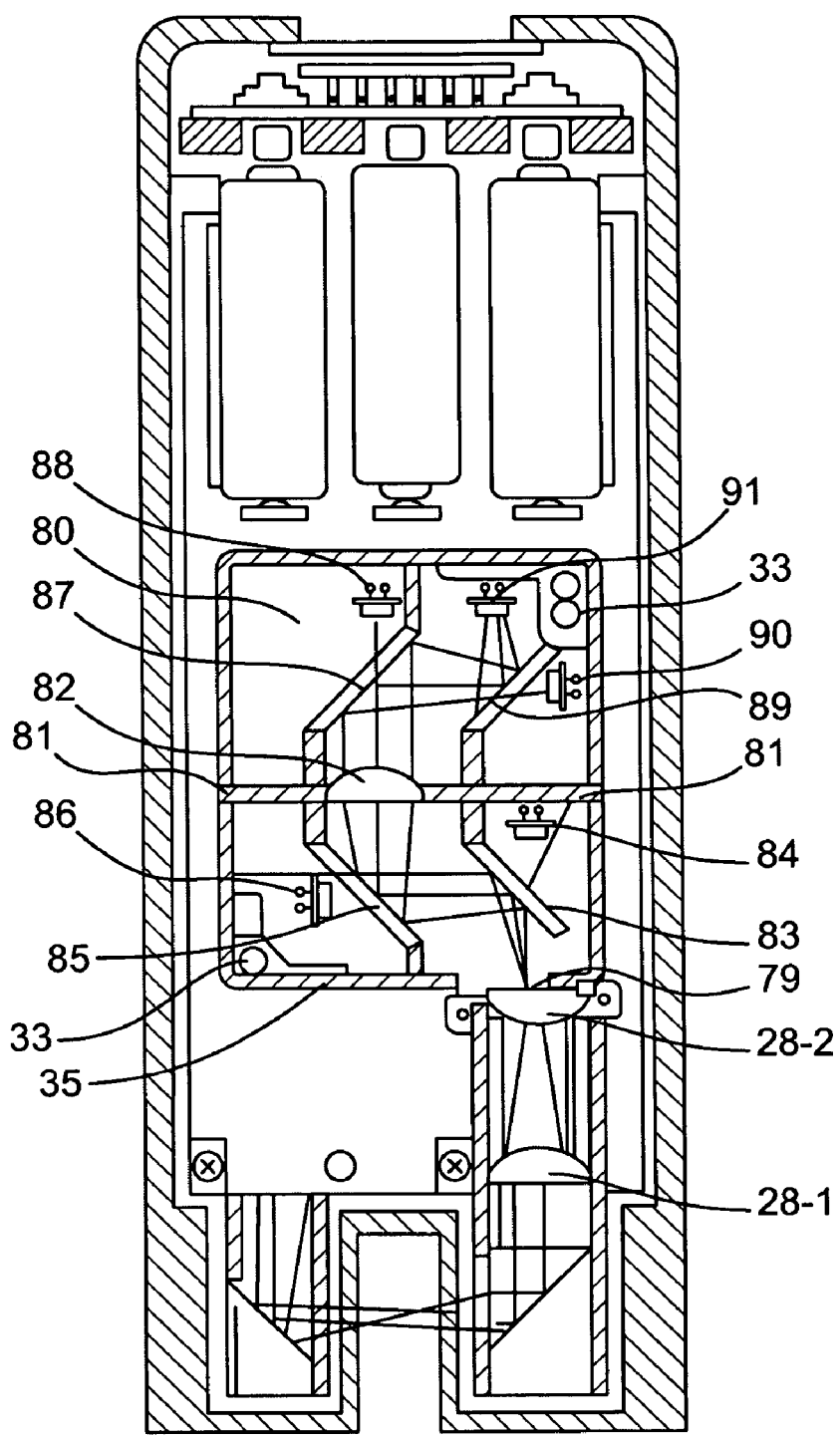
FIG. 15 shows a third embodiment of the handheld ultraviolet spectrometer of the invention which applies a four-piece UV filter in the UV wavelength separation system of the ultraviolet spectrometer.

FIG. 15 shows a third embodiment of the handheld ultraviolet spectrometer 1000. This embodiment replaces the flat mirror 74, the astigmatic mirror (toroidal mirror) 75, the variable wavelength optical UV filter 76, the pair of UV filter mounts 77, and the linear detector array 78 in FIG. 14 with optically opaque walls 81, a positive lens 82, four (4) optical filters (a diameter of 12.7 mm made by Lambda Research Optics, Inc., Costa Mesa, Calif.), and five (5) UV detectors (a diameter of 9.1 mm, model no. PDU-C105-Q made by Photonic Detector Inc., Camarillo, Calif.). The four optical filters include a first optical filter 83 with a maximum transmission at 288 nm for a 45 degree angle, a second optical filter 85 with a maximum transmission at 296 nm for a 45 degree angle, a third optical filter 87 with a maximum transmission at 312.5 nm for a 45 degree angle, and a forth optical filter 89 with a maximum transmission at 365 µm for a 45 degree angle. Each of the optical filter may be an interference filter which has a thin transparent spacer placed between two semi-reflective coatings so as to use multiple reflections and interference to select a narrow frequency band. The five UV detectors include a first UV detector 84 for measuring UV intensity at 288 nm, a second UV detector 86 for measuring UV intensity at 296 nm, a third UV detector 88 for measuring UV intensity at 312.5 nm, a forth UV detector 90 for measuring UV intensity at 365 nm, and a fifth UV detector 91 for measuring UV intensity at 254 nm.

The center of the first optical filter 83 is aligned with the axis of the second cylinder 26, while the body of the first optical filter 83 is positioned at a 45-degree angle from an axis of the second cylinder 26. The second optical filter 85 is positioned parallel with the first optical filter 83 and with its center corresponding to center of the first optical filter 83. The body of the positive lens 82 is arranged perpendicular to the axis of the second cylinder 26 with its center corresponding to the center of second optical filter 85. The third optical filter 87 is positioned perpendicular to the second optical filter 85 and with its center corresponding to center of the second optical filter 85 as well as the center of the positive lens 82. The fourth optical filter 89 is positioned parallel with the third optical filter 87 and with its center corresponding to center of the third optical filter 87. The four optical filters and the positive lens 82 are supported by the opaque walls 81 to maintain the relative positions. The five UV detectors are positioned at a 45-degree angle from a respective optical filter, and with its center corresponding to the center of the respective optical filter.

Inside the UV wavelength selector 80, the UV light passes via the input diaphragm 79 as in FIG. 14, then partially passes via the first optical filter 83 to the first UV detector 84 and partially being reflected to the second optical filter

85. The UV light reaches the second optical filter 85 then partially passes there though to the second UV detector 86 and partially being reflected to the third optical filter 87. The UV light reflected by the second optical filter 85 passes thought the positive lens 82 to be focused to the detector 91 The UV light reaches the third optical filter 87 then partially passes there though to the third UV detector 88 and partially being reflected to the fourth optical filter 89. The UV light reaches the fourth optical filter 89 then partially passes there though to the fourth UV detector 90 and partially being reflected to the fifth optical detector 91. Output signals from the optical detectors are different for different photodiodes because of not uniform intensity distribution in the light sources. Each light source has its individual preamplifier with various amplification according to a level of signal from the specific detector. The optical detectors may be commercially available photodiodes.

The embodiment of FIG. 15 has more components than the embodiment of FIG. 14 but cost less since the photodiodes are cheaper than the linear detector array 78. In addition, the photodiodes and the optical filters are much easier to orient with respect to one another than the components in FIG. 14. However, the photodiodes and the optical filters are oriented with respect to one another for a particular sample solution only. The embodiment of FIG. 15 cannot be adapted to other sample solutions as the embodiments of FIGS. 7 and 14. For different components to be analyzed, a specific set of filters are assembled. The total accuracy and sensitivity for variants with the photodiodes and the optical filters can be 5 to 10 times higher than the embodiment depicted in FIG. 14, and the sensor can work with a UV source of a lower intensity. It is possible because the input diaphragm 79 and the sensitive area of the optical detectors 84, 86, 88, 90, 91 can be several mm$^2$, wherein the input slits 36 and one individual element of the detector array 39 or 78 is usually fewer than 0.5 mm$^2$.

Figure 16:
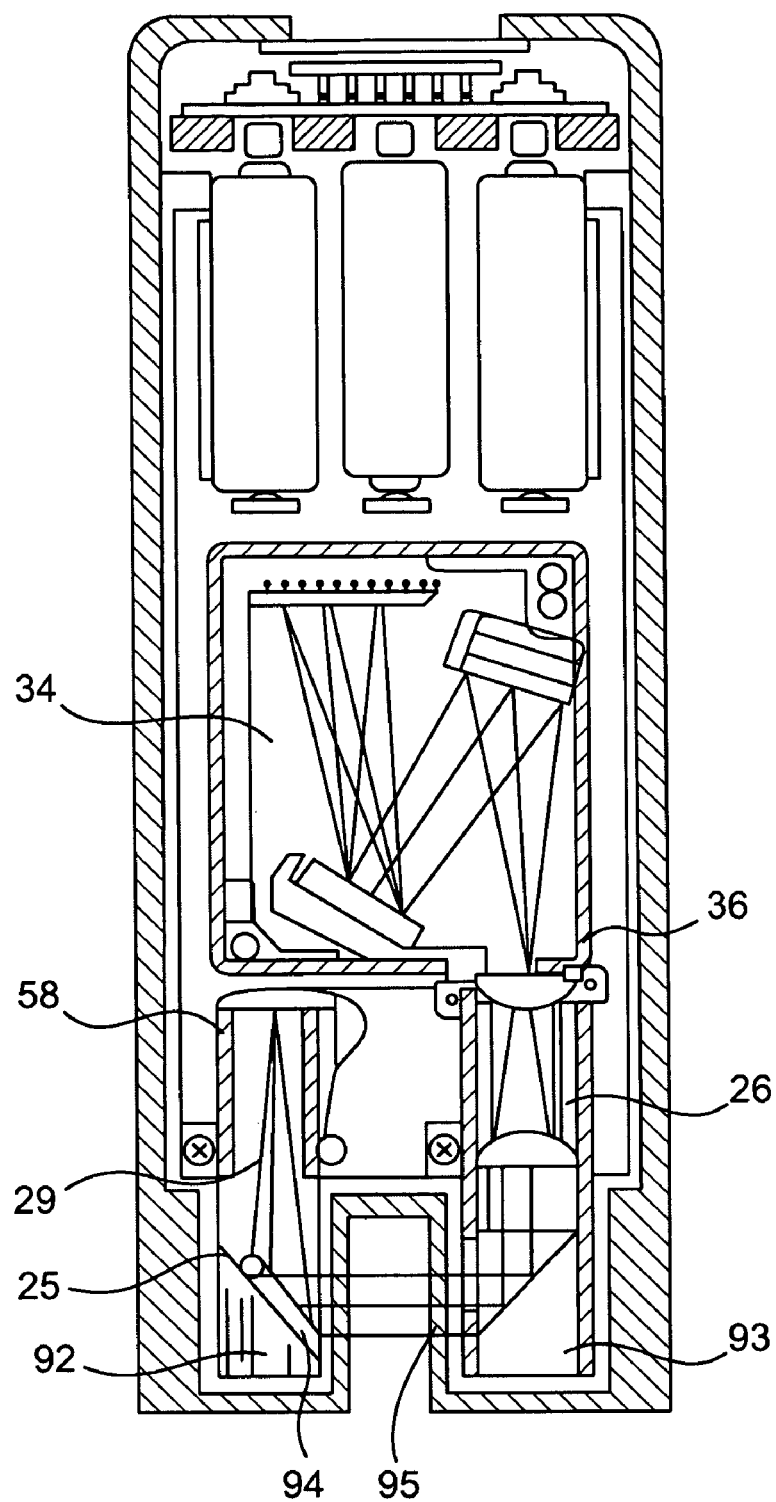
FIG. 16 shows a fourth embodiment of the handheld ultraviolet spectrometer of the invention which applies off-axis parabolic mirrors as focusing means in first and second cylinders of the ultraviolet spectrometer.

FIG. 16 shows a fourth embodiment of the handheld ultraviolet spectrometer 1000 of the invention which applies off-axis parabolic mirrors as focusing means in the first and second cylinders 25, 26. This embodiment replaces the first and second prismatic mirrors 27, 57 in FIG. 7 with a first parabolic mirror 92, and a second parabolic mirror 93 respectively, and replaces the input window 16 and the output window 18 in FIG. 7 with a first flat window 94 and a second flat window 95 respectively. The three positive lenses 28-1, 28-2, 28-3 (shown in FIG. 7, FIG. 10 and FIG. 14) and the spacers 30, 29, 55, 56 (shown at FIG. 7 and FIG. 10) are also not required in the embodiment. That makes optics and mechanics cheaper in producing this embodiment. This embodiment is easier in assembling because off-axis parabolic mirrors 92 and 93 can be permanently glued into the cylinders 25 and 26. Its adjustment is easier because the cylinder 26 with the second parabolic mirror 93 can be rotated until the maximum signal achieved, and can then be secured by the cylinder holders 31

Figure 17A:
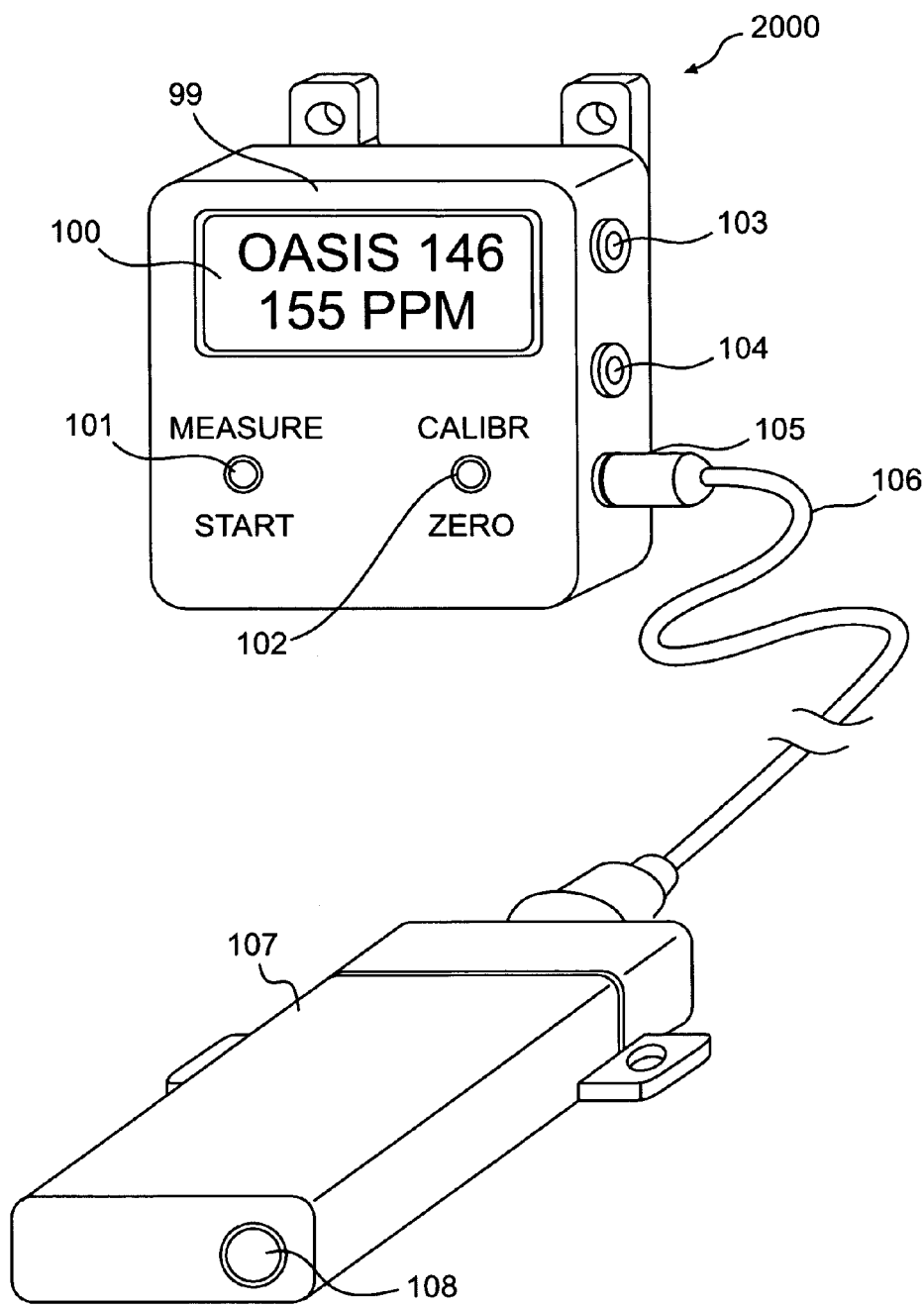
FIG. 17A shows a perspective view of a two-part ultraviolet spectrometer 2000 of the invention.
Figure 17B:
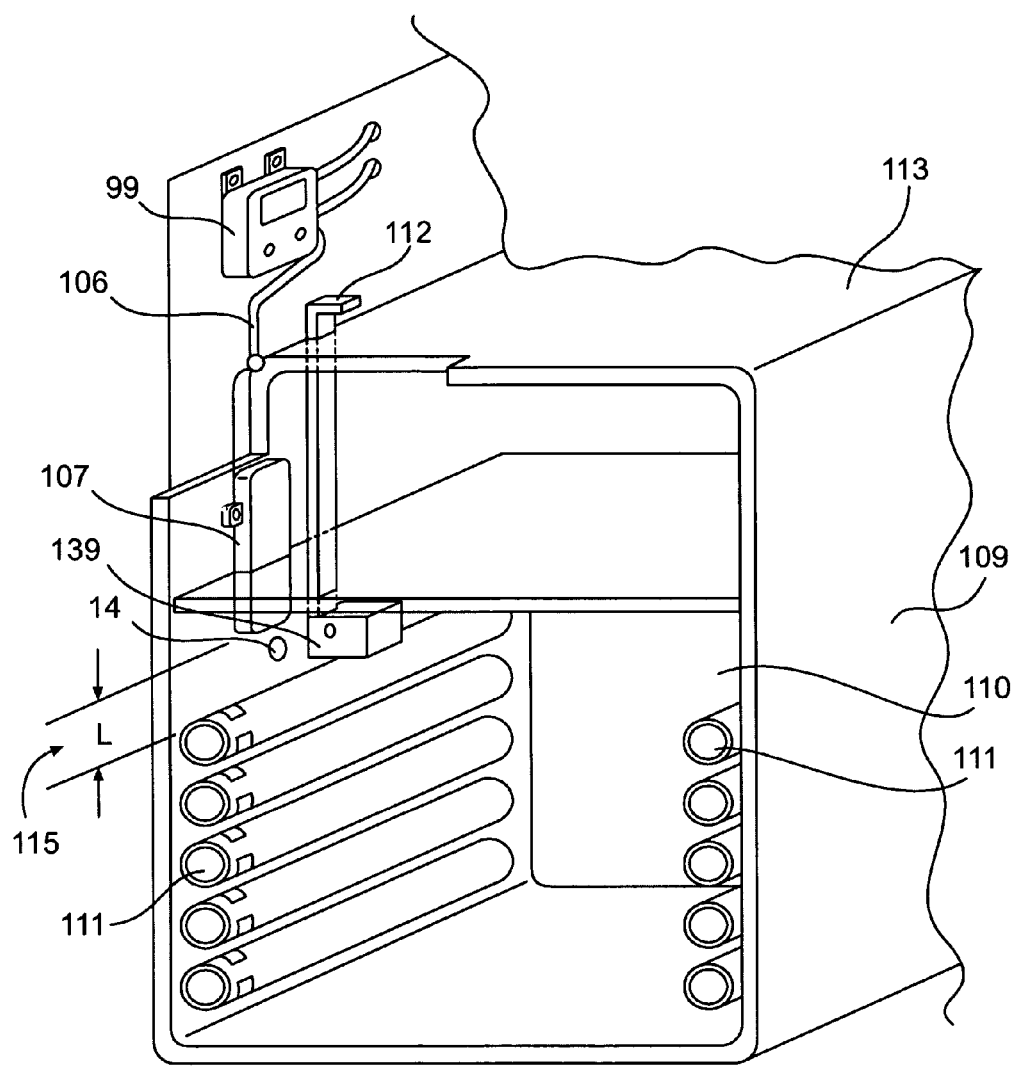
FIG. 17B shows a sanitizing system combining chemical disinfection with UV disinfection.

FIG. 17A shows a perspective view of a two-part ultraviolet spectrometer 2000 of the invention. The two-part embodiment has a wall-mounted controller unit 99 and a dip sensor unit 107. The wall-mounted controller unit 99 includes a display 100, a "START" button 100, and a "ZERO" button 102 which function similarly to those of the handheld model depicted in FIG. 11. The wall-mounted controller unit 99 further includes a power connector 103, an RS-232 connector 104, a sensor connector 105, and a sensor cable 106 which links to the sensor unit 107. Unlike the handheld model depicted in FIG. 7 with an input window 16 and an output window 18, the sensor unit 107 has only an input window 18, while the UV light sources is immersed in a sanitizing solution 110 in a sanitizing chamber 109 as shown in FIG. 17B. FIG. 17B shows a sanitizing system combining chemical sanitizing with UV sanitizing. In this embodiment, the UV light is not only used for testing the detergent residuals in the sanitizing solution 110, but also used for killing microorganisms such as bacteria in the sanitizing solution 110. In the system 2000, assemblies 111 of quartz sleeves with UV lamps positioned on the walls of the sanitizing chamber 109 supply the UV light. A distance 115 of 10 mm-30 mm is left between a top lamp and the input window 108 to preserve an analytical area 114. The sanitizing chamber 109 has a lid 113 to protect users from dangerous UV radiation. The lid 113 has a sealed opening for the cable 106 and an actuator 112. The actuator 112 allows safely rotating a zeroing chamber 139 into the analytical area 114 and out of the area during measurements without opening the lid 113. The UV lamps 111 produce a high level of UV radiation such that they cannot be used without adequate protection.

UV energy penetrates the outer cell membrane, passes through the cell body, and disrupts its DNA, preventing reproduction. UV treatment does not alter water chemically; nothing is being added except energy. The sterilized microorganisms are not removed from the water. UV disinfections do not remove dissolved organics, inorganics, or particles in the water. The degree of inactivation by ultraviolet radiation is directly related to the UV dose applied to the water. The dosage, a product of UV light intensity and exposure time, is measured in microwatt second per square centimeter ($\mu$ws/cm2). Most UV units are designed to provide a dosage greater than 30,000 $\mu$ws/cm2 after one year of continuous operation. Notice that UV does not effectively disinfect some organisms (most molds, protozoa, and cysts of *Giardia lamblia* and *Cryptosporidium*) since they require a higher dose.

Figure 17C:
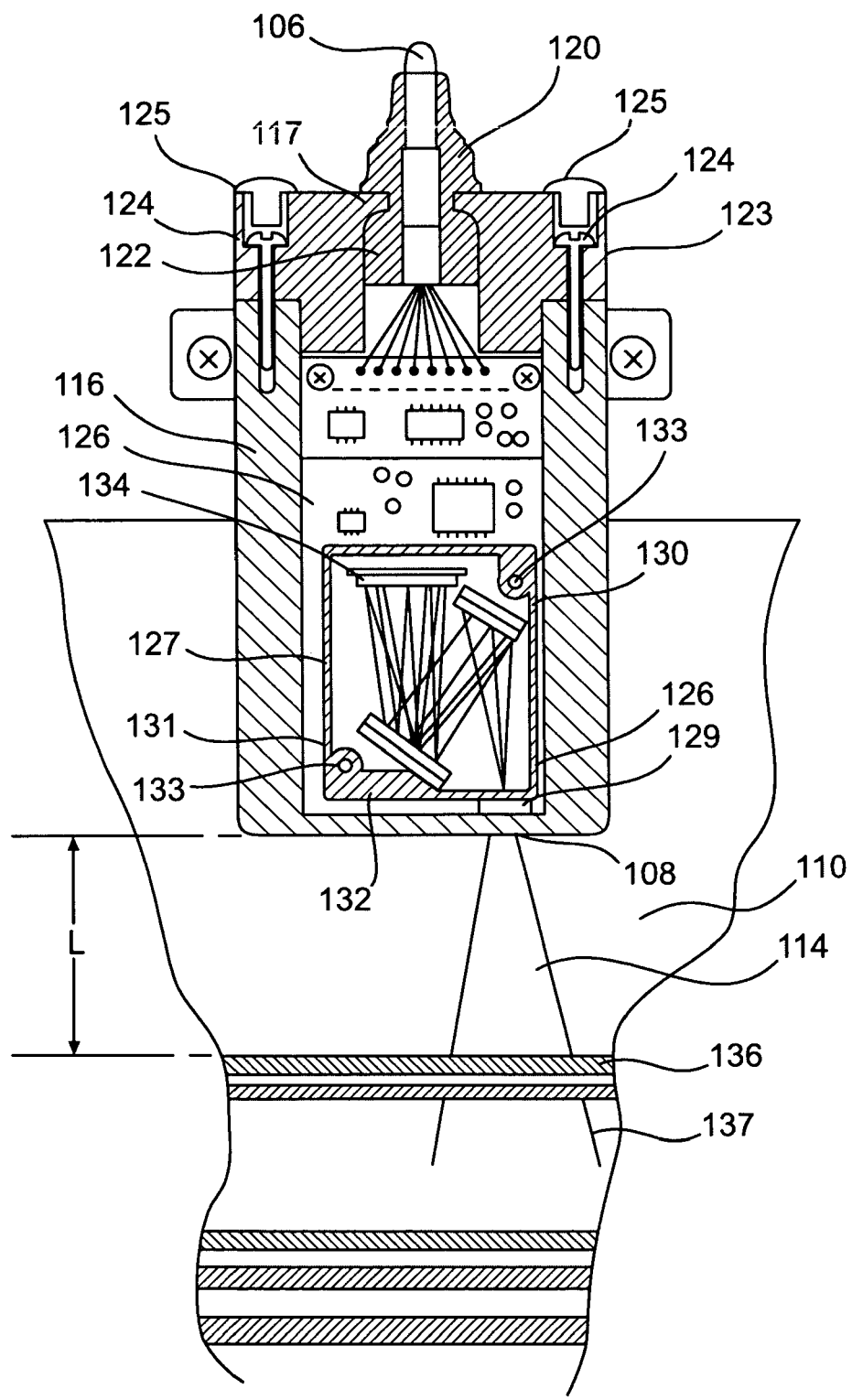
FIG. 17C shows a cross-sectional view of the sensor unit 107.

FIG. 17C shows a cross-sectional view of the sensor unit 107. The sensor unit 107 includes a sensor housing 116, a sensor lid 117, the input window 108 for UV beam, a strain relief 120, the sensor cable 106, an epoxy fitter 122, an o-ring 123, screws 124, rubber plugs 125, a sensor printed board 126, an UV wavelength separation system 127, a wavelength adjustment screw 132, threaded holes 133 for mounting screws. The UV wavelength separation system 127 is similar to the UV wavelength separation system 34 in FIG. 7, and includes an input slit 128, an optical diaphragm 129 for limiting an angle view, a holographic diffraction gratings 130, a flat mirror 131, and a detector array 134. A quartz sleeve 136 with a UV lamp 137 therein is positioned under the input window 108 to preserve an analytical area 114.

Figure 17D:
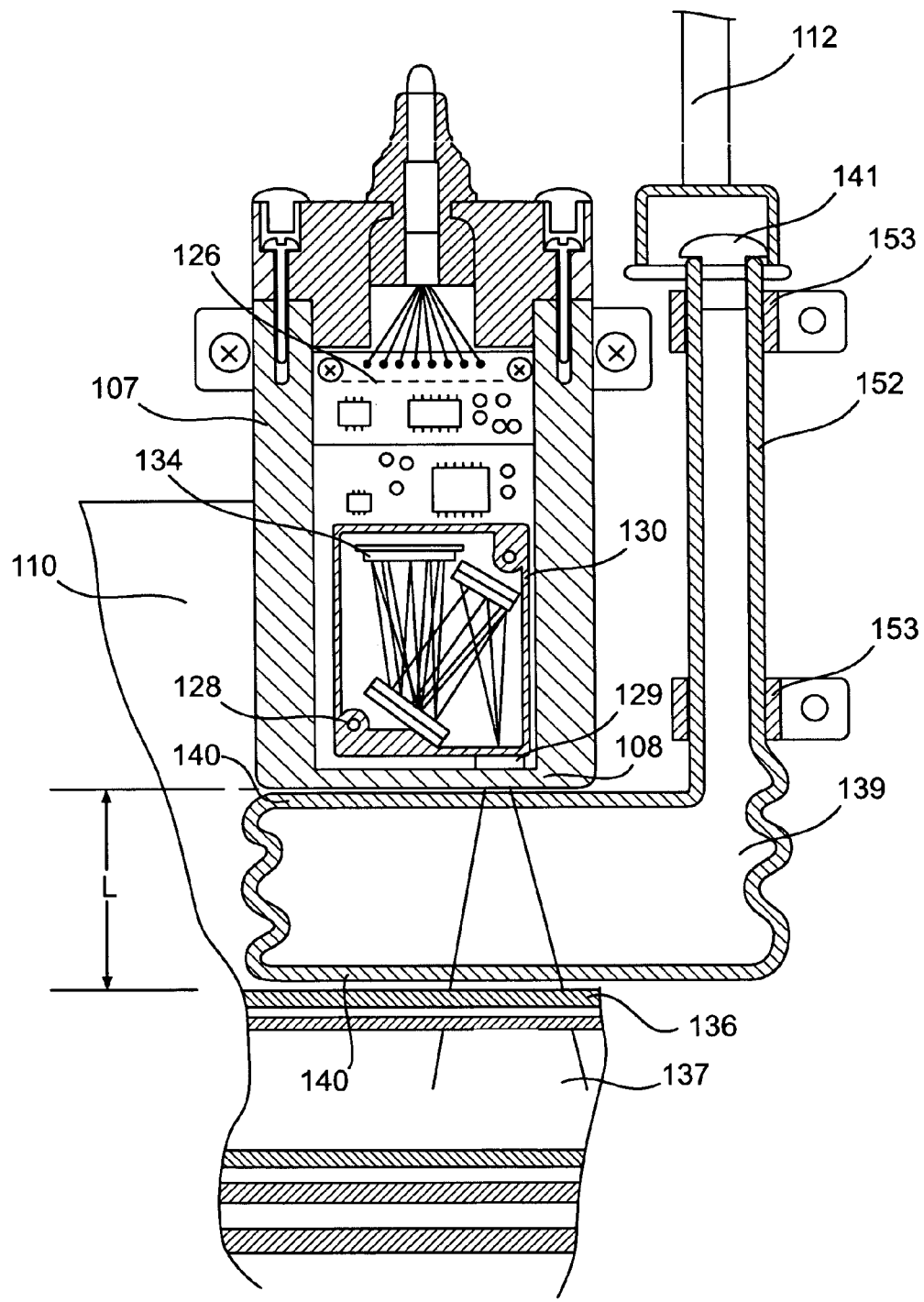
FIG. 17D shows the system 200 undergoing a periodical zeroing procedure with zero water. The periodical zeroing procedure is performed after each cleaning procedure.

FIG. 17D shows the system 200 undergoing a periodical zeroing procedure with zero water. The periodical zeroing procedure is performed after each cleaning procedure. A zeroing chamber 139 is first filled with water through a tube 152, plugged with a zeroing chamber plug 141 and then the zeroing chamber 139 is secured with mounting brackets 153 but accommodating a possibility of rotation. During a zeroing procedure, the chamber can be rotated with the actuator 112 in a position between the quartz sleeve 136 and the sensor unit 107. The zeroing chamber 139 has flexible walls to adjust its dimensions to actual dimensions between the quartz sleeve 136 and the sensor unit 107. The zeroing chamber 139 has a pair of optical windows 140 with a diameter from 10 mm to 25 mm. The UV light from the UV lamp 137 passes through the zero water to the input slit 128. Signals for all wavelengths are measured and saved in memory for calculating optical densities during measuring. Then the zeroing chamber 139 is rotated out of the analytical area 114

The ultraviolet spectrometer can transmit and receive data externally, and can be controlled remotely. The ultraviolet spectrometer can be attached to a tool or applicator device for controlling the mixing, dispensing, or release of surface active, antimicrobial, pesticide, or lubricating agent onto a surface or into the air.

The invention may be used for controlling the mixing, dispensing or application of chemicals to prepare, dispense a cleaning, antimicrobial, lubricating, or pesticidal composition into a solution, onto a surface, or into the air.

The invention may be used for interrupting or terminating the operation of a mixer, dispenser, or applicator based on the measured concentration (or lack thereof) of surface-active agent, antimicrobial agent, pesticide, or lubricant.

The invention may be used for monitoring a cleaning, antimicrobial, pesticidal, or lubricating process to determine if said agents are present in or removed from the process.

The invention may be used for measuring or monitoring cleaning, antimicrobial pesticide or lubricant chemicals, compositions and products in mixing, production, packaging, transportation (trucks, ships, planes, cars) and storage areas for safety.

The invention may be used for measuring or monitoring surface active or antimicrobial agents in processing and cooling waters, including but not limited to: cooling towers, flumes, chillers, pulp and paper processing, oil drilling.

The invention may be used for monitoring surface active, or antimicrobial agents in discharge and waste water from including, but not limited to: vehicle and fleet washing, food and beverage processing, laundry, warewashing, surface cleaning, third-sink sanitizing, airplane toilets treatments, aseptic packaging.

The invention may be used for measuring or monitoring surface active, or antimicrobial agents in drinking water to include, but not limited to: municipal water processing and water supplies, water lines, bottled water, dental lines.

The invention may be used for measuring or monitoring antimicrobial agents in liquid or gaseous phase for regulatory or compliance purposes.

The invention may be used for evaluating or monitoring of compatibility of ingredients in a cleaning, antimicrobial, pesticide, or lubricant composition, or material compatibility with packaging materials.

The invention may be used for measuring or monitoring the concentration of surface active, antimicrobial, pesticide or lubricant agents in a process as an out of product indicator.

The invention may be used for monitoring a cleaning or antimicrobial process by measuring or monitoring the change in concentration of surface active agent or antimicrobial.

The invention may be used for measuring or monitoring the concentration of surface active, antimicrobial, pesticide, or lubricating agent in flowing and stationary bodies of water to include, but not limited to: lakes, reservoirs, rivers and streams, pools, spas, fountains, recreational water.

The invention may be used for measuring or monitoring surface active or antimicrobial agents during the cleaning and antimicrobial processing of filtration membranes used in liquid- and gas-phase separations and purifications to include, but not limited to those used in: dairy processing, dialysis, wastewater treatment, sludge processing, water purification, purification and separation of gases.

The invention may be used for measuring or monitoring the application of antimicrobial agents onto foods, food contact surfaces, and non-food contact surfaces.

The invention may be used for measuring and monitoring the application of lubricants to a surface.

The invention may be used for measuring and monitoring the application of surface active or antimicrobial agents for aseptic packaging.

The principles, preferred embodiments and modes of operation of the present invention have been described in the foregoing specification. However, the invention, which is intended to be protected, is not limited to the particular embodiments disclosed. The embodiments described herein are illustrative rather than restrictive. Variations and changes may be made by others, and equivalents employed, without departing from the spirit of the present invention. Accordingly, it is expressly intended that all such variations, changes and equivalents that fall within the spirit and scope of the present invention as defined in the claims, be embraced thereby.

What is claimed is:

1. A UV absorption spectrometer comprising:
   a housing, a controller, and a sensor unit including an ultraviolet light source, an analytical area in an analytical cell or in running water or gaseous medium, and an UV wavelength separator including a UV detector, wherein
   an ultraviolet light in a wavelength range of 200-320 nm emits from the light source through the analytical area to the wavelength separator, and
   the controller transforms output signals from the UV detector into absorbance values or optical densities for two or more wavelengths in the wavelength range, calculates differences of said absorbance values or optical densities, determines a concentration of a chemical in the solution with calibration constants found for a known concentration of the chemical and said differences of said absorbance values or optical densities,
   wherein the UV wavelength separator includes at least one optical filter comprising an interference filter having a thin transparent spacer placed between two semi-reflective coatings so as to use multiple reflections and interference to select a narrow frequency band.

2. The UV absorption spectrometer according to claim 1, wherein the chemical is a biocide.

3. The UV absorption spectrometer according to claim 1, wherein the solution is a sanitizing solution, and the chemical is a quaternary ammonium cation (quat).

4. The UV absorption spectrometer according to claim 1, wherein the ultraviolet light source is a gas discharge lamp, a mercury lamp, a deuterium lamp, a metal vapor lamp, a light emission diode, or a plurality of light emission diodes.

5. The UV absorption spectrometer according to claim 1, wherein the ultraviolet light source is a mercury low pressure lamp with a main line at about 254 nm, or a Krypton gas discharge lamp.

6. The UV absorption spectrometer according to claim 1, further comprising another ultraviolet detector for monitoring an intensity of the ultraviolet light source.

7. The UV absorption spectrometer according to claim 1, wherein the analytical cell is a sample cell, a flow cell, or an open path cell.

8. The UV absorption spectrometer according to claim 1, wherein the housing includes a first cylinder which accommodates the UV light source and a first optical means for directing and focusing the light emitted by the UV light source towards the analytical area, a second cylinder which accommodates the UV detector and a second optical means for directing and focusing the light passing via the analytical area towards the UV detector, axes of the first and second cylinders are arranged in parallel while perpendicular to a light traveling path in the analytical area.

9. The UV absorption spectrometer according to claim 8, wherein the first optical means include a first prismatic mirror, and the second optical means include a second prismatic mirror, two lenses, and two spacers.

10. The UV absorption spectrometer according to claim 8, further comprising another UV detector for measuring turbidity which is positioned inside of the housing, between the first cylinder and the second cylinder, and right on top of the analytical area thereby receiving scattered radiation from the analytical area.

11. The UV absorption spectrometer according to claim 8, wherein the UV wavelength separator includes an input slit and the input slit is symmetrically aligned with the axis of the second cylinder,
   a receiving surface of the UV detector is positioned perpendicular to the axis of the second cylinder,
   a center of the spherical mirror is aligned with the axis of the second cylinder, while a bottom of the spherical mirror is positioned at a 20 degree angle from the axis of the second cylinder, and
   a center of the diffraction grating corresponds to the center of the spherical mirror such that the diffraction grating reflects UV light of different wavelengths under different angles to produce a linear spectrum on the UV detector.

12. The UV absorption spectrometer according to claim 8, wherein the UV detector is a linear detector array, and the UV wavelength separator includes a flat mirror, an astigmatic/toroidal mirror, a variable wavelength optical UV filter, a pair of UV filter mounts, and an input diaphragm.

13. The UV absorption spectrometer according to claim 12, wherein the input diaphragm is symmetrically aligned with the axis of the second cylinder,
   a receiving surface of the linear detector array is positioned perpendicular to the axis of the second cylinder,
   a center of the flat mirror is aligned with the axis of the second cylinder, while a bottom of the flat mirror is positioned at a 20-degree angle from the axis of the second cylinder, and
   a center of the astigmatic/toroidal mirror corresponds to the center of the flat mirror such that the flat mirror directs UV light from the input diaphragm to the astigmatic/toroidal mirror 75 which transforms light from a circular input diaphragm into the line on the sensitive surface of the linear detector array.

14. The UV absorption spectrometer according to claim 8, further including a first optical filter with a maximum transmission at 288 nm for a 45 degree angle, a second optical filter with a maximum transmission at 296 nm for a 45 degree angle, a third optical filter with a maximum transmission at 312.5 nm for a 45 degree angle, and a fourth optical filter with a maximum transmission at 365 nm for a 45 degree angle, and
   further including a first UV detector for measuring UV intensity at 288 nm, a second UV detector for measuring UV intensity at 296 nm, a third UV detector for measuring UV intensity at 312.5 nm, a fourth UV detector for measuring UV intensity at 365 nm, and a fifth UV detector for measuring UV intensity at 254 nm.

15. The UV absorption spectrometer according to claim 14, further including a positive lens, and wherein
   a center of the first optical filter is aligned with the axis of the second cylinder, while a body of the first optical filter is positioned at a 45-degree angle from the axis of the second cylinder,
   the second optical filter is positioned parallel with the first optical filter, the second optical filter having a center corresponding to a center of the first optical filter,
   a body of the positive lens is arranged perpendicular to the axis of the second cylinder with a center thereof corresponding to the center of second optical filter,
   the third optical filter is positioned perpendicular to the second optical filter, the third optical filter having a center corresponding to a center of the second optical filter as well as a center of the positive lens,
   the fourth optical filter is positioned parallel with the third optical filter, the fourth optical filter having a center corresponding to a center of the third optical filter, and
   each of the UV detectors are positioned at a 45-degree angle from a respective optical filter, each UV detector having a center corresponding to a center of the respective optical filter.

16. The UV absorption spectrometer according to claim 8, wherein the first and second optical means include off-axis parabolic mirrors.

17. The UV absorption spectrometer according to claim 1, wherein the controller is included in a controller unit which includes a power supply, a memory, a display, and a keypad.

18. The UV absorption spectrometer according to claim 1, further comprising a sensor connector, wherein the controller is included in a wall-mounted controller unit, the sensor unit is a dip sensor unit for dipping into a sanitizing chamber, and the sensor connector connects between the controller unit and the sensor unit.

19. The UV absorption spectrometer according to claim 18, further comprising assemblies of quartz sleeves with UV lamps positioned on walls of the sanitizing chamber for UV sanitation.

20. The UV absorption spectrometer according to claim 1, wherein the UV detector is a UV array detector which includes UV photodiodes, UV photomultipliers, a CCD array, or a photodiode array.

21. A method for measuring a chemical concentration in a solution comprising:
   providing a near UV spectrometer with a sample chamber, the ultraviolet spectrometer comprising an ultraviolet light source emitting light in a wavelength range of 200-320 nm, an UV wavelength separator including a UV detector, and a controller;
   providing a liquid or gaseous medium into the sample chamber;
   using the ultraviolet spectrometer to measure values or optical densities for two or more wavelengths in the wavelength range;
   programming the controller to calculate differences of said absorbance values or optical densities, and to determine a concentration of the chemical in the sample chamber with calibration constants found for a known concentration of the chemical and said differences of said absorbance values or optical densities,
   wherein the solution is a sanitizing solution, the chemical is a detergent, and the controller calculates and determines based upon equations:

$$y = 178.16 \cdot x - 14.608 \cdot x^2 + 0.5726 \cdot x^3 - 0.0081 \cdot x^4$$

where $y = \dfrac{\text{Concentration of detergent, } ppm}{\text{Concentration of sanitizer, } ppm}$ $x = (\text{Position of minimum, nm} - 230 \text{ nm})$ the % is a ratio of the detergent to a sanitizer contained in the sanitizing solution.

22. The method according to claim 21, wherein the UV light source is a mercury lamp, and the controller calculates and determines based upon equations:

$$C_{quat}=2852 \cdot Z(s) \cdot (1-0.042 \cdot Z(s)^2)$$

$$Z(s)=(D_{254}(s)-2.62 \cdot D_{280}(s)+1.62 \cdot D_{296}(s))$$

$$D_{254}(s) = \log\left(\frac{U_{254}(0)}{U_{254}(s)}\right)$$

is an optical density at the wavelength 254 nm $$D_{280}(s) = \log\left(\frac{U_{280}(0)}{U_{280}(s)}\right)$$

is an optical density at the wavelength 280 nm $$D_{296}(s) = \log\left(\frac{U_{296}(0)}{U_{296}(S)}\right)$$

is an optical density at the wavelength 296 nm wherein $U_{254}(0)$, $U_{280}(0)$ and $U_{296}(0)$ are intensities of ultraviolet signals at wavelengths of 254 nm, 280 nm and 296 nm during zeroing, and $U_{254}(s)$, $U_{280}(s)$ and $U_{296}(s)$ are intensities of ultraviolet signals at wavelengths 254 nm, 280 nm and 296 nm during measuring.

23. The method according to claim 21, wherein the UV light source is a krypton lamp or a deuterium lamp, and the controller calculates and determines based upon equations:

$$C_{quat}=2450 \cdot (D_{259}(s)-D_{275}(s))$$

where $C_{quat}$ is an actual concentration of chemicals, $$D_{259}(S) = \log\left(\frac{U_{259}(0)}{U_{259}(s)}\right)$$

is an optical density at the wavelength 259 nm $$D_{275}(S) = \log\left(\frac{U_{275}(0)}{U_{275}(s)}\right)$$

is an optical density at the wavelength 275 nm, $U_{259}(0)$ and $U_{275}(0)$ is an intensity of ultraviolet signals at wavelengths 259 nm and 275 nm during zeroing, and $U_{259}(0)$ and $U_{275}(0)$—is an intensity of ultraviolet signals at wavelengths 259 nm and 275 nm during measuring.

24. The method according to claim 21, further comprising: measuring turbidity of the liquid or gaseous medium, and compensating for turbidity influence on the determined chemical concentration.

25. The method according to claim 24, wherein the controller calculates a compensated concentration value $C_{comp}$ based upon equations:

$$C_{comp}=C_{meas}-K_t \cdot U_t(s)$$

$C_{meas}$ is a not-compensated output concentration value.
$U_t(s)$ is an output of a turbidity channel $$K_t = \frac{C_{meas}(T_{st})}{U_t(T_{st})}$$

is a compensation coefficient, where $C_{meas}(T_m)$ is a not-compensated output concentration value, and $U_t(T_{st})$ is an output of a turbidity channel during calibration when calibration solution has a known turbidity $T_{st}$ and zero concentration of sanitizer.

26. The method according to claim 21, further comprising: sanitizing the sample chamber with UV light.

27. The method according to claim 21, further comprising: monitoring an intensity of the ultraviolet light source.

28. A method comprising:
measuring an optical density at each of a plurality of near ultraviolet (UV) wavelengths of a sample of a sanitizing solution, the sanitizing solution having an unknown concentration of an antimicrobial agent and an unknown concentration of a detergent;
determining which one of the plurality of the near UV wavelengths corresponds to a minimum of the measured optical densities of the sample;
determining a ratio of detergent to antimicrobial agent for the sample based on the determined one of the plurality of wavelengths and a calibration curve of ratio of detergent to antimicrobial agent versus wavelength;
determining a maximum of the measured optical densities of the sample;
determining an actual concentration of the antimicrobial agent in the sample based on the determined maximum of the measured optical densities of the sample; and
determining an actual concentration of the detergent in the sample based on the determined ratio of detergent to antimicrobial agent and the actual concentration of the antimicrobial agent.

29. The method of claim 28 further comprising:
measuring an optical density at each of a plurality of near UV wavelengths of a plurality of control solutions, each of the plurality of control solutions having a known concentration of the antimicrobial agent and each of the plurality of control solutions having a different known concentration of the detergent; and
generating the calibration curve of ratio of detergent to antimicrobial agent versus wavelength based on the measured optical densities for the plurality of control solutions.

30. The method of claim 28 wherein the antimicrobial agent is a quaternary ammonium cation (quat).

31. The method of claim 28 wherein measuring an optical density at each of a plurality of near UV wavelengths of a plurality of control solutions comprises measuring an optical density at each of a plurality of wavelengths between about 220 nm and 290 nm of a plurality of control solutions.

32. The method of claim 28 wherein measuring an optical density at each of a plurality of near UV wavelengths of a sample of a sanitizing solution comprises measuring an optical density at each of a plurality of near UV wavelengths between about 220 nm and 290 nm of a sample of the sanitizing solution.

33. The method of claim 28 wherein determining which one of the plurality of the near UV wavelengths corresponds to a minimum comprises determining which one of the plurality of the near UV wavelengths between about 255 nm and 275 nm corresponds to a minimum of the measured optical densities of the sample.

34. The method of claim 28 wherein determining a maximum of the measured optical densities comprises determining a maximum of the measured optical densities of the sample in range between about 255 nm and 275 nm.

35. An apparatus comprising:
an analytical cell that holds a sample of a sanitizing solution having an unknown concentration of an antimicrobial agent and an unknown concentration of a detergent;
a light source that emits near ultraviolet (UV) light into the analytical area;
a detector that receives the emitted near UV light transmitted through the sample; and
a controller that determines an optical density of the sample at each of a plurality of the near UV wavelengths based on the light received by the detector, determines which one of the plurality of the near UV wavelengths corresponds to a minimum of the measured optical densities of the sample, determines a ratio of detergent to antimicrobial agent for the sample based on the determined one of the plurality of wavelengths and a calibration curve of ratio of detergent to antimicrobial agent versus wavelength, determines a maximum of the measured optical densities of the sample, determines an actual concentration of the antimicrobial agent in the sample based on the determined maximum of the measured optical densities of the sample, and determines an actual concentration of the detergent in the sample based on the determined ratio of detergent to antimicrobial agent and the actual concentration of the antimicrobial agent.

* * * * *